(12) United States Patent
Kurthy

(10) Patent No.: US 9,662,187 B2
(45) Date of Patent: May 30, 2017

(54) HYDRAULIC PRESSURE DENTAL IMPRESSION

(71) Applicant: Evolve Dental Technologies, Inc., Irvine, CA (US)

(72) Inventor: Rodger Kurthy, Irvine, CA (US)

(73) Assignee: Evolve Dental Technologies, Inc., Irvine, CA (US)

( * ) Notice: Subject to any disclaimer, the term of this patent is extended or adjusted under 35 U.S.C. 154(b) by 108 days.

(21) Appl. No.: 14/156,216

(22) Filed: Jan. 15, 2014

(65) Prior Publication Data

US 2014/0199653 A1    Jul. 17, 2014

Related U.S. Application Data

(60) Provisional application No. 61/753,187, filed on Jan. 16, 2013.

(51) Int. Cl.
*A61C 9/00*    (2006.01)

(52) U.S. Cl.
CPC .................................. *A61C 9/0006* (2013.01)

(58) Field of Classification Search
CPC ..................................................... A61C 9/0006
See application file for complete search history.

(56) References Cited

U.S. PATENT DOCUMENTS 3,882,601 A * 5/1975 Jahn ........................ A61C 9/00
                                                                    433/214
4,378,211 A * 3/1983 Lococo ................ A61C 9/0006
                                                                    433/36

(Continued)

FOREIGN PATENT DOCUMENTS

DE    19526017 C1    8/1996
RU    2200502 C2    3/2003
(Continued)

OTHER PUBLICATIONS

International Search Report and Written Opinion of related patent application PCT/US2014/011717 dated May 1, 2014 (15 pages).
PCT Search Report and Written Opinion in PCT application No. PCT/US2015/040163 mailed Oct. 1, 2015 in 8 pages.

*Primary Examiner* — Ralph Lewis
(74) *Attorney, Agent, or Firm* — Knobbe, Martens, Olson & Bear, LLP

(57) ABSTRACT

In an exemplary embodiment, a method of creating an impression of structures of the human oral cavity comprises: preparing impression trays; creating a first, or base, impression; grinding out portions of the base impression; and using the void(s) in the ground out base impression to take a second, or wash, impression. The base impression is taken with an excess of a high-density impression material which is positioned to extend beyond the structures of interest (of which the impression is being taken). The base impression is removed and all fine structure surrounding the structure(s) of interest is ground out. A wash impression is then taken using a low-density impression material. The base impression creates a seal around the structure(s) of interest (a closed system), thereby producing omnidirectional hydraulic pressure on the low-density material. Such omnidirectional hydraulic pressure produces a highly detailed final impression from which a high-quality model (e.g., cast) can be made.

19 Claims, 34 Drawing Sheets

(56) References Cited

U.S. PATENT DOCUMENTS

| | | | | |
|---|---|---|---|---|
| 4,382,785 A * | 5/1983 | Lococo | ................ | A61C 9/0006 |
| | | | | 433/36 |
| 5,382,164 A | 1/1995 | Stern | | |
| 5,607,628 A | 3/1997 | Palazzolo | | |
| 6,116,905 A | 9/2000 | Hoos | | |
| 6,196,840 B1 * | 3/2001 | Zentz | ................... | A61C 9/0006 |
| | | | | 433/214 |
| 8,591,228 B2 * | 11/2013 | Neuschafer | .......... | A61C 9/0006 |
| | | | | 249/54 |
| 8,939,763 B2 * | 1/2015 | Tropmann | ........... | A61C 9/0006 |
| | | | | 433/37 |
| 2006/0172253 A1 * | 8/2006 | Pumphrey | ................ | A61C 9/00 |
| | | | | 433/37 |
| 2007/0054237 A1 * | 3/2007 | Neuschafer | .......... | A61C 9/0006 |
| | | | | 433/37 |
| 2009/0274999 A1 | 11/2009 | Coopersmith | | |
| 2012/0219925 A1 | 8/2012 | Tropmann | | |
| 2013/0101954 A1 * | 4/2013 | Riedel | ..................... | A61K 6/10 |
| | | | | 433/37 |
| 2015/0010879 A1 | 1/2015 | Kurthy | | |
| 2015/0173867 A1 * | 6/2015 | Mahn | ................... | A61C 9/0026 |
| | | | | 433/214 |

FOREIGN PATENT DOCUMENTS

| | | |
|---|---|---|
| RU | 2458654 C2 | 8/2012 |
| SU | 1194408 A | 11/1985 |

\* cited by examiner

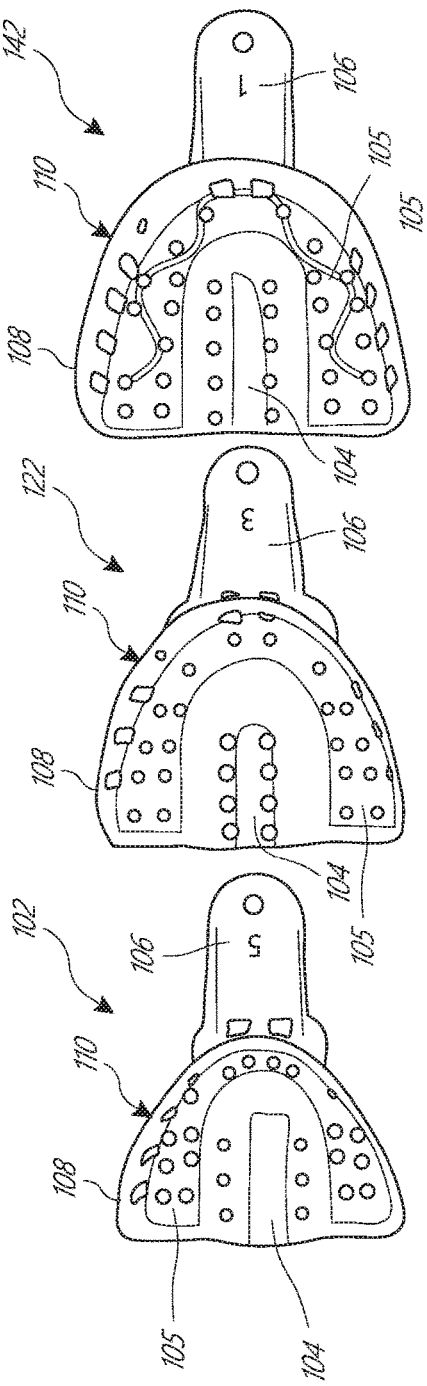
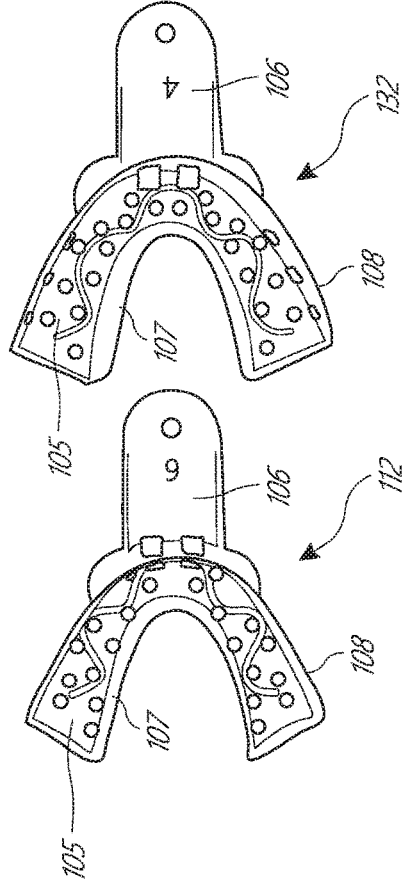

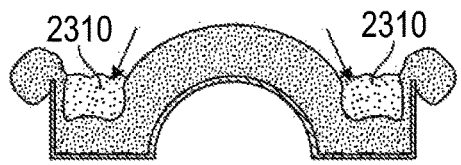
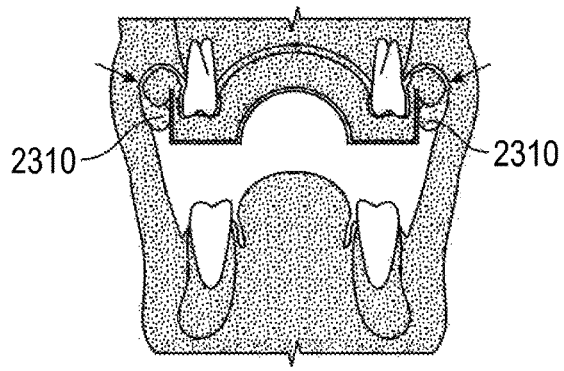
FIG. 32A  FIG. 32B
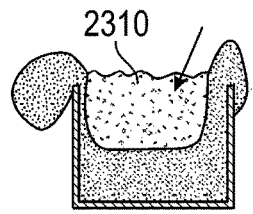 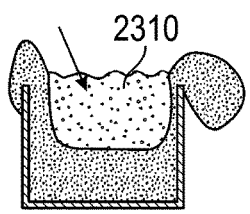
FIG. 32C
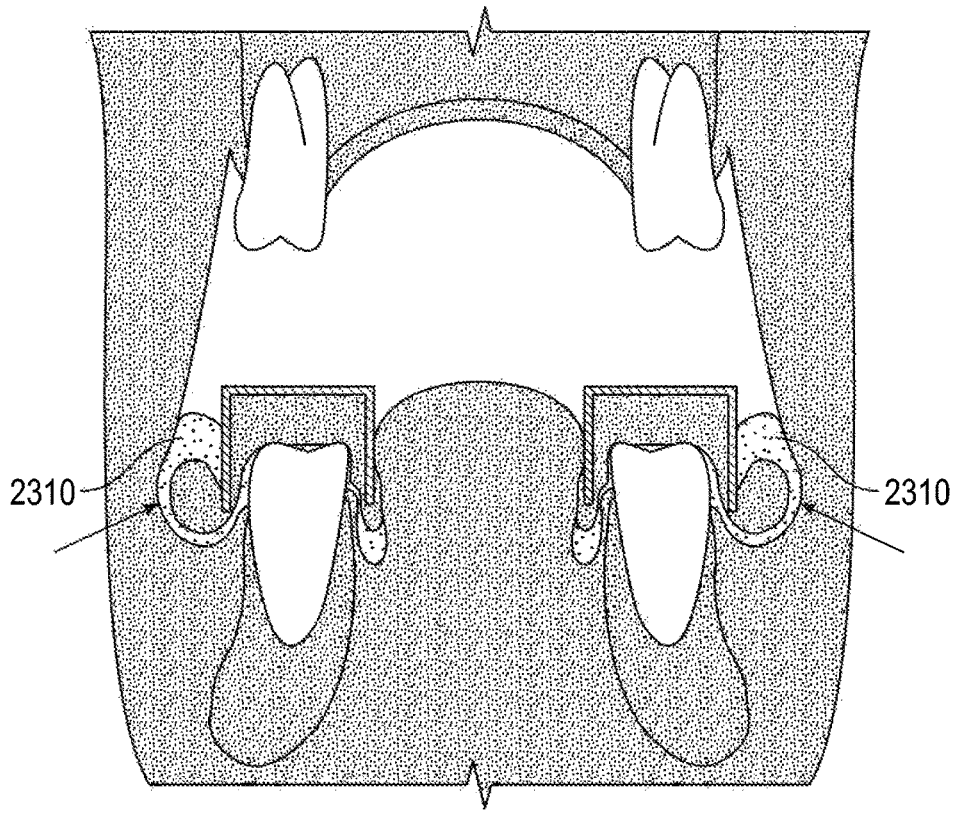
FIG. 32D

HYDRAULIC PRESSURE DENTAL IMPRESSION

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The present invention relates to devices, systems and methods for dental impressions. More specifically, the present invention relates to devices, systems and methods for creating hydraulic pressure formed dental impressions.

Description of the Related Art

Requirements for the fabrication of many types of dental products (e.g., dental trays, orthodontic appliances, crowns, bridges, implants, study models, etc.) can be highly exacting. Therefore, these dental products require highly sophisticated and detailed molding procedures capable of capturing the required detail of the relevant oral structures. Currently used dental impression techniques create predominantly unidirectional vertical pressure and consequently do not consistently capture sufficiently detailed reproductions of certain oral structures. Another problem with these dental impression techniques is that they can allow the formation of bubbles and voids, typically called pulls, on and in the impressions. The presence of such bubbles and pulls in impressions, particularly in critical areas of the oral impressions, renders the impression useless and necessitates that the impression be taken again, thereby increasing, among other things, the required time, materials, patient time, doctor time, and overall cost. Commonly used techniques are particularly ill-adapted to capture slight or highly detailed structures, including but not limited to the small but very sharp crevice at the junction of the teeth and gums, generally known as the gingival crevice.

Accordingly, there is a need for improved devices, systems and methods for creating more detailed dental impressions.

SUMMARY OF THE INVENTION

In accordance with one embodiment, a method of producing an impression of a portion of an object is provided. The method comprises: taking a first impression of the object using a first impression material; removing a detail from the first impression of the object; placing a second impression material inside the first impression of the object; and taking a second impression of the object using the first impression of the object containing the second impression material. When taking the first impression, the first impression material is caused to extend past the portion of an object of which an impression is being taken (or the area of interest). Additionally, the detail that is removed corresponds to a detail of the portion of the object of which an impression is being taken.

In accordance with another embodiment, a method of producing an impression of a tooth or teeth is provided. The method comprises: providing an impression tray; providing a first impression material; filling the impression tray with the first impression material; taking a first impression of the tooth or teeth (using the impression tray filled with the first impression material) to create a cavity corresponding to a dimension of the tooth or teeth; enlarging a dimension of the cavity; providing a second impression material; filling the first impression of the tooth or teeth with the second impression material; and taking a second impression of the tooth or teeth to create a cavity corresponding to a dimension of the tooth or teeth. When taking the first impression, the first impression material is forcibly caused to extend beyond the tooth or teeth. The second impression of the tooth or teeth is taking using the first impression of the tooth or teeth, after the cavity has been enlarged in at least one dimension, filled with the second impression material.

In accordance with another embodiment, a system for casting a mold of a tooth or teeth is provided. The system comprises: an impression of the tooth or teeth created using a first impression step and a second impression step, and a casting material. The first impression step used to create the impression of the tooth or teeth includes: filling an impression tray with a first impression material; taking a first impression of the tooth or teeth to create a cavity corresponding to the tooth or teeth; forcibly pushing the first impression material into an oral structure extending beyond the at least one tooth; removing the first impression; and enlarging at least one dimension of the cavity. The second impression step used to create the impression of the tooth or teeth includes: filling the first impression with a second impression material; taking a second impression of the tooth or teeth to create a cavity corresponding to the tooth or teeth; and removing the second impression. The second impression step is accomplished using the first impression filled with the second impression material.

In accordance with another embodiment, a kit for creating a hydraulic pressure dental impression is provided. The kit includes: an impression tray; a first impression material having a first density; a second impression material having a second density; and a bur configured to grind set, or hardened, impression material. The density of the second impression material is lower than the density of the first impression material.

BRIEF DESCRIPTION OF THE DRAWINGS

FIGS. 1A-1F illustrate various sizes of impression trays that may be used in some embodiments of the present invention. FIGS. 1A, 1C, and 1E illustrate various impression trays for taking impressions of the teeth of the upper jaw while FIGS. 1B, 1D, and 1F illustrate various impression trays for taking impressions of the teeth of the lower jaw.

FIG. 13A shows a base impression of the teeth of an upper jaw. FIG. 13B shows a base impression of the teeth of a lower jaw.

FIG. 18A shows a base impression of the teeth of an upper jaw. FIG. 18B shows a base impression of the teeth of a lower jaw.

FIG. 27A shows an impression being taken of the teeth of the upper jaw and FIG. 27B shows an impression being taken of the teeth of the lower jaw.

FIG. 28A shows an impression being taken of the teeth of the upper jaw and FIG. 28B shows an impression being taken of the teeth of the lower jaw.

FIGS. 32A and 32C illustrate cross-sectional views of base impressions, taken using conventional impression techniques, that have been filled with wash impression material.

FIGS. 32B and 32D illustrate cross-sectional views of the wash impression material-filled base impressions of FIGS. 32A and 32C placed in the mouth according to conventional technique.

DETAILED DESCRIPTION OF PREFERRED EMBODIMENTS

Figure 2A:
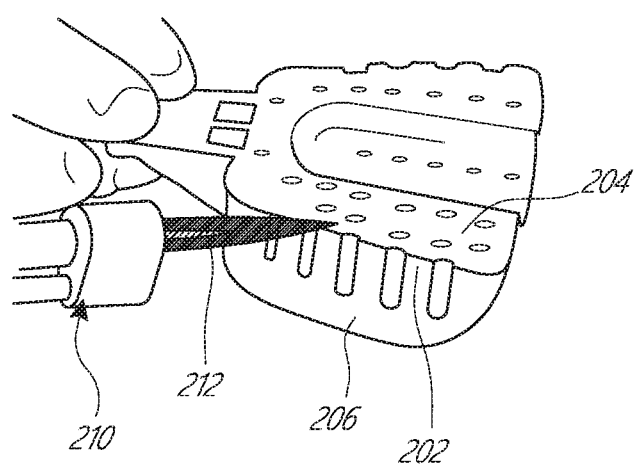
FIGS. 2A-2B illustrate modification of impression trays, such as those illustrated in FIGS. 1A-1F.

The hydraulic pressure dental impression technique is a two-step impression using a first impression (e.g., a base impression), taken as a first separate step, then a second impression (e.g., a wash impression), taken as a second separate step. Hydraulic pressure dental impressions may be used any time a dental impression is necessary where hard structures, such as teeth and/or dental implants, are present in the mouth. In some embodiments, hydraulic pressure dental impressions can be used for any of the following, but is not limited to the following: crowns, bridges, indirect restorations (e.g., inlays and onlays, etc.), tooth veneers (e.g., porcelain veneers and composite veneers, etc.), dental models, study models, orthodontic impressions for any type of orthodontic case (e.g., conventional orthodontics, short term orthodontics, clear aligner orthodontics, etc.), teeth whitening trays, athletic mouth guards, appliances used to reduce or protect from teeth grinding (e.g., bruxism), appliances used to treat tempero-mandibular disorders (e.g., TMJ/TMD), appliances used to prevent headaches, appliances used to treat snoring, appliances used to treat sleep apnea, and appliances used to hold or retain medications in place over the teeth to treat any condition of the teeth, gums or any other oral structures.

First, a base impression must be taken. The base impression will generally be taken using a heavier, stiffer, or more viscous type of material. The base impression can be taken using any type of impression putty or heavy body impression material. In some embodiments, the base impression can be taken using one of two impression materials, including KöR® Putty (regular or fast set) or KöR® Heavy Body.

Preparation for the Base Impression

To prepare for taking the base impression, any visible supragingival calculus buildup/accumulation may be removed to advantageously allow for a more detailed and/or more accurate impression of the desired structures. In some embodiments, a full prophylaxis is performed. After performing a full prophylaxis including removal of subgingival calculus, or if the gingiva is inflamed after the prophy, it can be desirable to wait for the passage of some period of time between the prophy and the impression to allow the aforementioned swollen or inflamed gingiva to heal and shrink to allow for a more detailed and/or more accurate impression of the desired structures, particularly of the gingival margin. Depending on the extent of "damage" and/or swelling or inflammation present, the period of time between the prophy and the impression may be in the range of about 1-21 days, about 3-19 days, about 5-17 days, about 7-15 days, and about 9-13 days, or any other period of time needed for the tissues to heal and swelling/inflammation to subside. Some parameters on which the period of time between prophy and the impression may depend include, but are not limited to, the extent of inflammation and swelling (edema) of the gingival tissues and the extent of the gingival treatment (e.g., prophy, supragingival scaling, subgingival scaling, root planning, etc.).

Next, the proper size and type of impression tray must be selected. FIG. 1 is an illustration of varying sizes of rigid polycarbonate upper jaw impression trays and lower jaw impression trays. FIGS. 1A and 1B illustrate small upper rigid polycarbonate impression tray 102 and small lower rigid polycarbonate impression tray 112 respectively. FIGS. 1C and 1D illustrate medium upper rigid polycarbonate impression tray 122 and medium lower rigid polycarbonate impression tray 132 respectively. FIGS. 1E and 1F illustrate large upper rigid polycarbonate impression tray 142 and large lower rigid polycarbonate impression tray 152 respectively. FIGS. 1A, 1C, and 1E illustrate a common configuration for appropriate upper rigid polycarbonate impression trays, which may include an impression basket 110 and an impression tray handle 106. The impression basket 110 of the upper impression trays (small upper rigid polycarbonate impression tray 102, medium upper rigid polycarbonate impression tray 122, and large upper rigid polycarbonate impression tray 142) can include an impression tray outer retaining wall 108, an impression tray tooth trench 105, and a palate portion 104. As can be seen from the figures, the impression tray handle 106 attaches generally to the front of the impression tray tooth trench 105 and the impression tray outer retaining wall 108. Unlike upper impression trays, lower impression trays (small lower rigid polycarbonate impression tray 112, medium lower rigid polycarbonate impression tray 132, and large lower rigid polycarbonate impression tray 152, for example) have no palate portion 104. Rather, the lower impression trays have a cutout to accommodate oral structures, such as a tongue. Therefore, in addition to having an impression tray outer retaining wall 108 and an impression tray tooth trench 105, the lower impression trays may have an impression tray inner retaining wall 107. The lower impression trays may also have an impression tray handle 106. FIG. 1 illustrates only some embodiments of impression trays which may be used and is not intended to limit this disclosure in any way. Additional types and sizes of trays may be used, for example extra-large trays may be used and, as mentioned above, metal trays may be used. In some embodiments, the tray selected can be one size larger than would be normally used in an alginate impression to allow for a relatively loose fit within the mouth and around the teeth and gums. In some embodiments, rigid polycarbonate or metal impression trays are used. In other embodiments, any other type of impression tray can be used which is capable of holding the impression material and fitting loosely around the teeth.

Figure 2B:
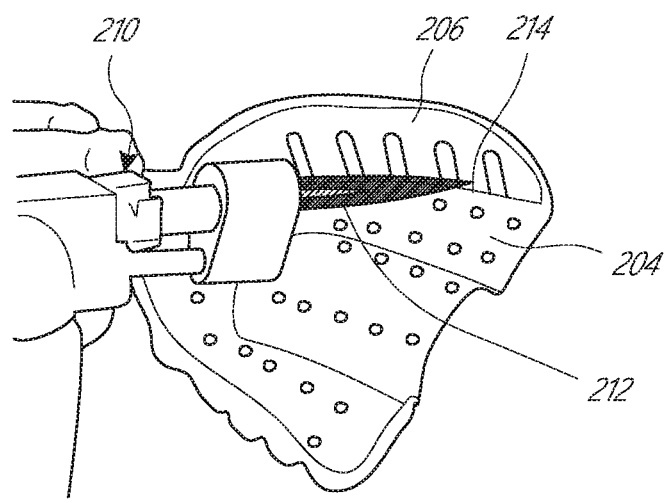

In embodiments in which rigid polycarbonate impression trays are used, such as those illustrated in FIGS. 1A-F, the rigid polycarbonate impression trays may be customized to better fit the oral cavities in question (i.e., upper and lower jaws of a patient). Areas which frequently benefit from such customization include, but are not limited to: the lingual flanges of lower trays (i.e., inner retaining wall 107), which may be moved toward the tongue; areas of lingual or palatal tori; and the posterior facial flanges (i.e., outer retaining wall 108) in the upper or lower molar regions, which may be made wider. Customization of rigid polycarbonate impression trays (or any other thermoplastic impression tray which becomes plastic and bendable upon heating) may be effected by localized application of heat. In some embodiments, a hand-held torch 210 may be used to selectively heat and consequently soften targeted regions of impression trays to allow for bending and modification/customization. FIGS. 2A and 2B illustrate the modification and customization of a rigid polycarbonate impression tray (such as those shown in FIGS. 1A-1F) using a hand-held torch 210 with a fine flame tip 212. First, the hand-held torch 210 is used to heat the impression tray along the outer edge 202 where the occlusal surface 204 of the tray joins/meets the facial or lingual side 206 of the impression tray (identified by the dashed line). The impression tray can also be heated along the inner edge 214 as shown in FIG. 2B where the occlusal surface 204 of the tray meets the facial side or lingual side 206 of the impression tray (identified by the dashed line). Heating on both the exterior side outer edge 202 as shown in FIG. 2A and the interior side inner edge 214 as shown in FIG. 2B can improve the evenness of customization. Upon heating, the entire side of the impression tray can be moved laterally (e.g., outward or inward), tilted (e.g., tilted outward or tilted inward), or moved laterally and tilted (e.g., moved outward and tilted outward, moved outward and tilted inward, moved inward and tilted inward, or moved inward and tilted outward). In some embodiments, customization may be effected in stages, for example: test the tray in the patient's mouth initially then customize; test the tray again in the patient's mouth and customize again any areas that are not sufficiently loose; continue until the patient can bite down fully on the tray without the tray impinging on soft tissues.

Figure 3A:
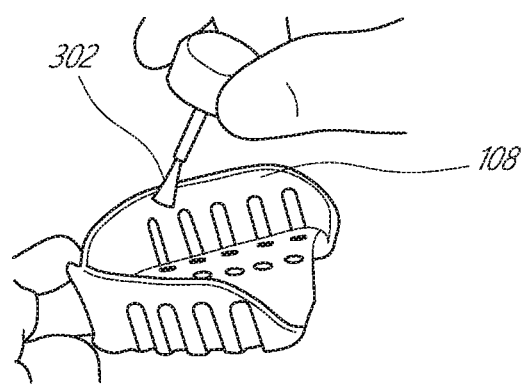
FIGS. 3A-3C illustrate the preparation of impression trays, including the application of impression tray adhesive.
Figure 3B:
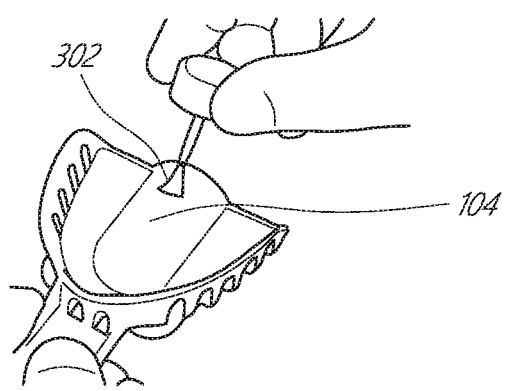
Figure 3C:
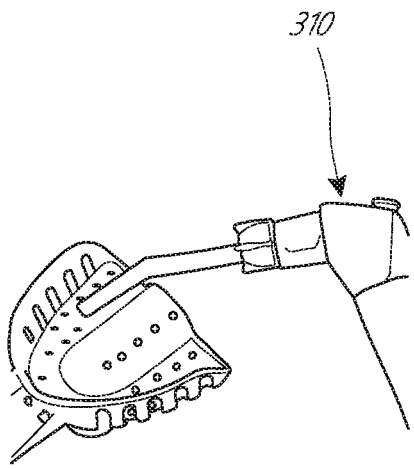

After preparing the impression trays, the trays can be further prepared by painting or coating them with an impression tray adhesive which can improve adhesion between the impression material and the impression tray. FIGS. 3A, 3B, and 3C illustrate the application and preparation of the impression tray adhesive. In some embodiments, the impression tray adhesive may be painted on in a very thorough thin coat (preferably without pooling). In other embodiments, the impression tray adhesive is applied in a heavy coat (again, preferably without pooling). In some embodiments, the impression tray adhesive is applied using an adhesive applicator brush 302 to all internal surfaces of the trays, up to and including the edges of the tray (the inner surface of the impression tray outer retaining wall 108) as shown in FIG. 3A and the entire palate portion 104 as shown in FIG. 3B. The impression tray adhesive can then be allowed to dry. In some embodiments, the impression tray adhesive is both air-thinned and air-dried as shown in FIG. 3C. The impression tray adhesive can be air-dried in ambient air for a time in the range of about 1-15 minutes, about 2-10 minutes, and 3-5 minutes, including about 3 minutes. In some embodiments, the air-drying time may be reduced by using an air spray 310 as shown in FIG. 3C. In some embodiments, impression tray adhesive is unnecessary, including, for example, embodiments in which metal trays covered with small holes are used to hold the impression material.

Figure 4A:
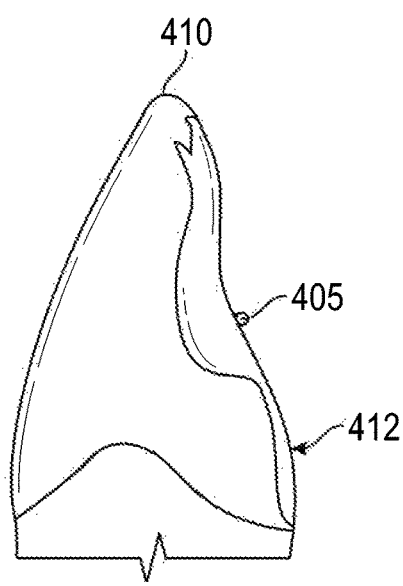
FIGS. 4A-4D illustrate cross-sectional views of resin being used to block out a fixed lingual retainer wire on the lingual surface of a tooth prior to taking an impression.
Figure 4B:
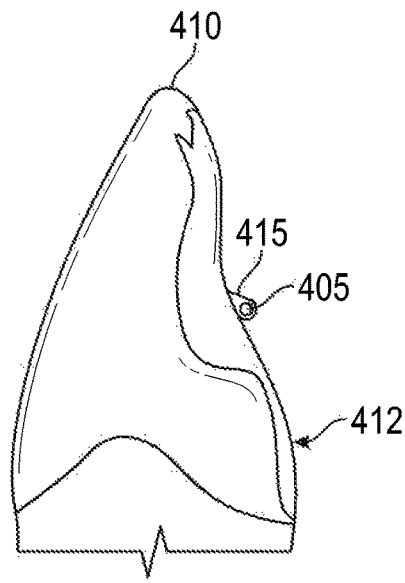
Figure 4C:
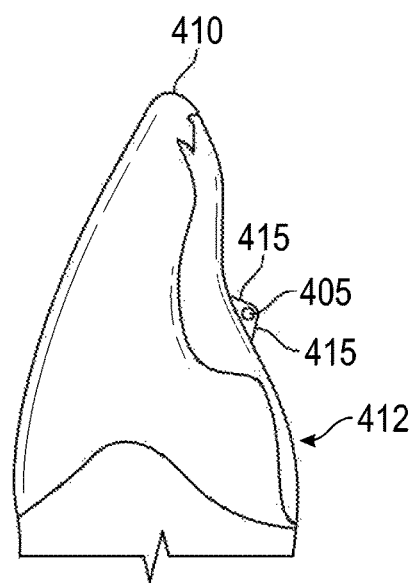
Figure 4D:
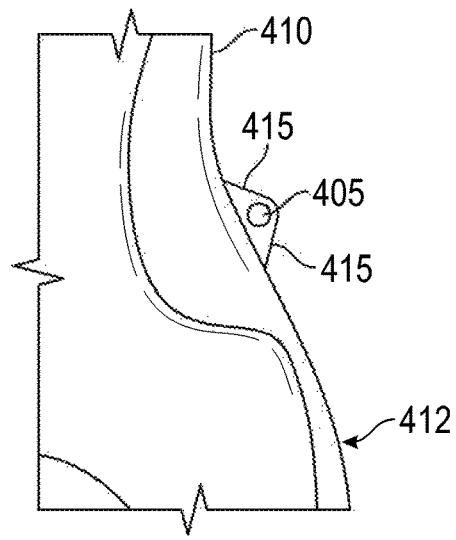

Once the impression trays have been prepared to accept the impression material, the patient's teeth can be prepared as needed. In some embodiments, open embrasures (e.g., the black triangles/openings between the teeth and gums) can be blocked out with flowable light cure composite resin. In these embodiments, the resin can be injected into the embrasure from the lingual side of the embrasure. In some embodiments, the resin can be kept within the confines of the lingual embrasure to advantageously ensure a proper and accurate impression. If resin extends onto the lingual surface of the teeth it can create a resin-based artifact in the material of the final impression (e.g., the hydraulic impression will accurately reflect the presence of the resin on the surface of the tooth/teeth). Patients having fixed lingual retainer wires may need additional attention and preparation. FIGS. 4A, 4B, 4C, and 4D illustrate the cross section of a tooth 410 having a fixed lingual retainer wire 405 on its lingual surface 412 and varying stages of resin blocking. FIG. 4A illustrates the cross section of a tooth 410 having a fixed lingual retainer wire 405. In some embodiments, the lingual embrasure spaces, or the spaces between the teeth (not shown), and/or the spaces directly under the fixed lingual retainer wire 405 may be filled with flowable light cure composite resin (known as "blocking out"). In other embodiments, the lingual embrasure spaces and/or the spaces directly under the fixed lingual retainer wire 405 may be filled with resin paint-on dam material (e.g., resin gingival barrier material). In some embodiments, fixed lingual retainer wire 405 is blocked in the following manner: blocking material 415 (e.g., flowable light cure composite resin or paint-on dam material) is added above the fixed lingual retainer wire 405 such that it does not cover the entire fixed lingual retainer wire 405 (as is shown in FIG. 4B); next, blocking material 415 is added below the fixed lingual retainer wire 405 such that it does not cover the entire fixed lingual retainer wire 405 (as is shown in FIGS. 4C and 4D); blocking material 415 can be removed or added to ensure that the outer surface of the fixed lingual retainer wire 405 is left uncovered and that most of the lingual surface 412 of the tooth 410 remains exposed. In embodiments in which flowable light cure composite resin is used, the resin can be only partially cured and not set completely rigidly thereby advantageously facilitating later removal (after impression completion) which could be rendered difficult given full curing.

Taking the Base Impression

As mentioned above, the base impression will generally be taken using a heavier, stiffer, or more viscous type of material than the wash impression. The base impression can be taken using any type of impression putty or heavy body impression material. In other embodiments, the base impression can be taken using one of two impression materials, including KöR® Putty (regular or fast set) or KöR® Heavy Body. In some embodiments, it is preferable to take the base impression using an impression putty as opposed to an impression material because putty can be more easily manually packed into the vestibules of a patient which can thereby create a better seal for the later wash impression. A tighter sealed system can allow the creation of greater hydraulic pressure during a wash impression and consequently a more accurate wash impression.

Taking the Base Impression Using Impression Putty

Figure 5:
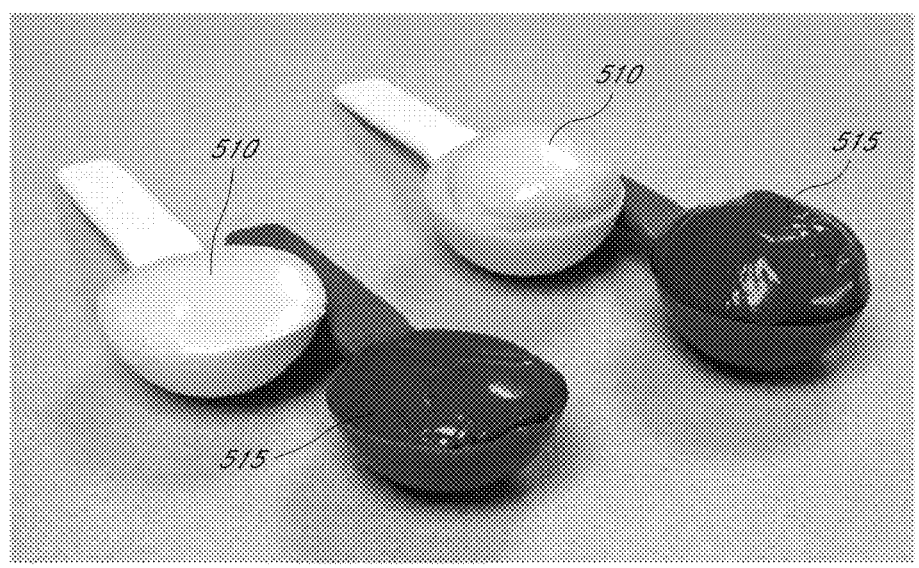
FIG. 5 illustrates a base portion of base impression putty and a catalyst portion of base impression putty which can be mixed to make base impression putty.
Figure 6A:
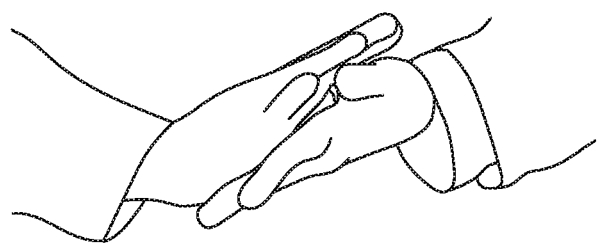
FIGS. 6A-6C illustrate the mixing of base portion of base impression putty and catalyst portion of base impression putty to make base impression putty.
Figure 6B:
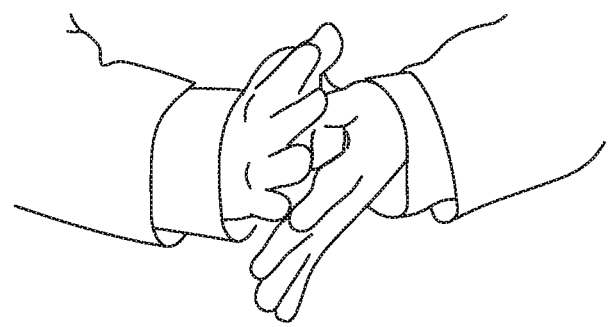
Figure 6C:
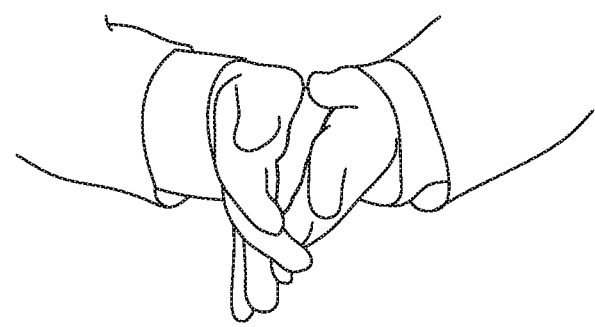
Figure 7A:
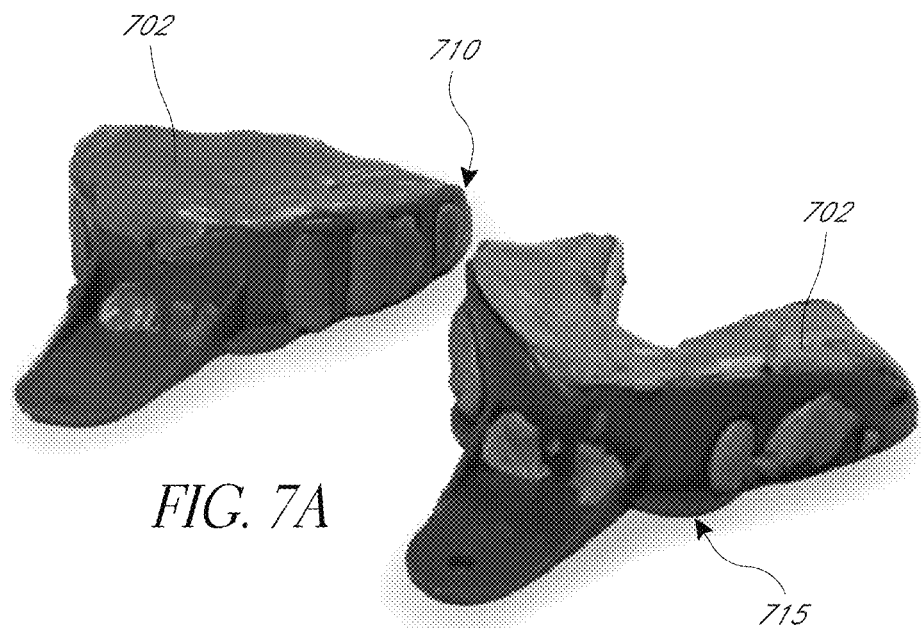
FIGS. 7A-7B illustrate impression trays, such as those shown in FIGS. 1A-1F, filled with impression putty, such as that shown in FIGS. 6A-6C.
Figure 7B:
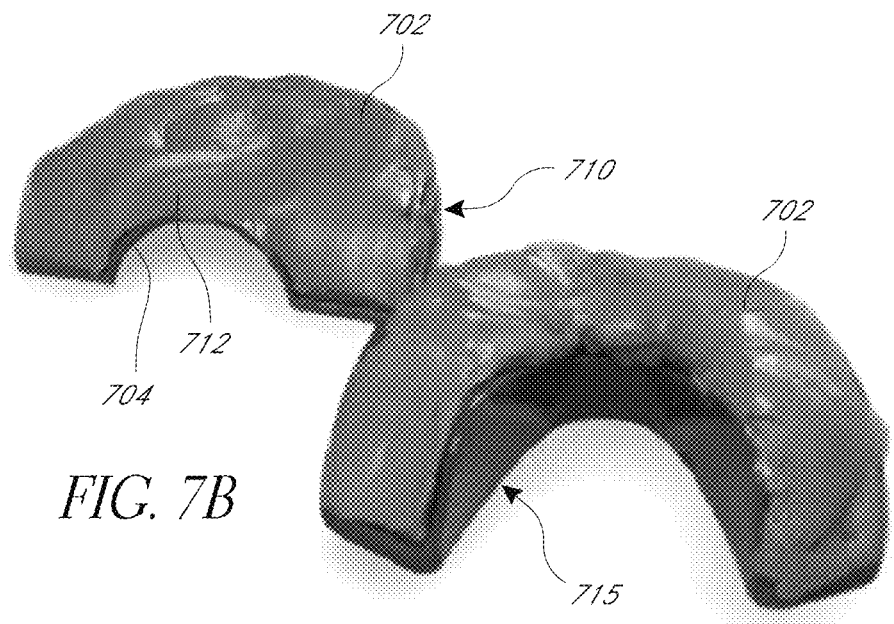

When using impression putty for the base material, prepare enough putty to fully load one impression at a time (e.g., upper or lower). It is generally not desirable to prepare more putty than required for a single impression because impression putties may set too quickly to successfully take more than a single impression at one time. In some embodiments, pre-made putty with two pre-putties may be used in which equal amounts of a base portion of base impression putty 510 and a catalyst portion of base impression putty 515 are mixed to make the impression putty (shown in FIG. 5). In these embodiments, pre-putty, including a base portion of base impression putty 510 and a catalyst portion of base impression putty 515, can be dispensed based on the size of the impression tray and amount of impression putty necessary for the particular impression (some impressions require more while others require less impression putty). The base portion of base impression putty 510 and catalyst portion of base impression putty 515 can then be mixed until they are substantially uniformly mixed (generally, for many commercial embodiments, this means until the putty has achieved a substantially uniform color). The putty may be mixed in any appropriate manner, including mechanically, manually. FIGS. 6A, 6B, and 6C illustrate one embodiment of mixing the two putties using the palms of the hands to roll and knead the putty until it is substantially uniformly mixed. After thorough mixing, fill the impression trays with the putty impression material. FIGS. 7A and 7B illustrate properly filled trays, including an upper tray 710 and a lower tray 715, from the front and rear respectively. Load sufficient putty 702 in the trays to ensure a full and complete impression. In some embodiments, a thin layer 712 of putty 702 fully covers the palate portion 704 of the upper tray 710 thereby advantageously securing the putty 702 to the tray (shown in FIGS. 7A and 7B). In some embodiments, the palate portion 704 of the upper tray 710 is not fully covered with putty 702 (not shown). In other embodiments, additional thickness of putty 702 can be placed over the palate portion 704 of the upper tray 710 (not shown).

Figure 8A:
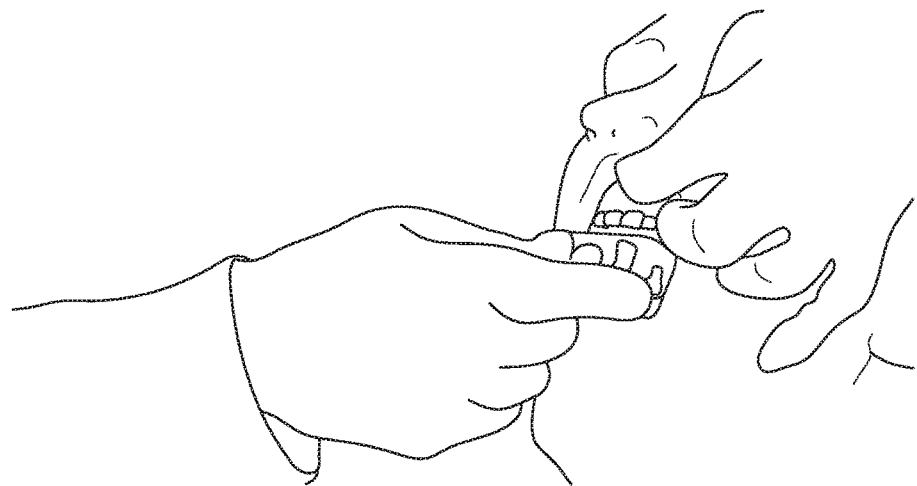
FIG. 8A illustrates placement of an impression tray filled with base impression putty, such as that shown in FIGS. 7A-7B.
Figure 8B:
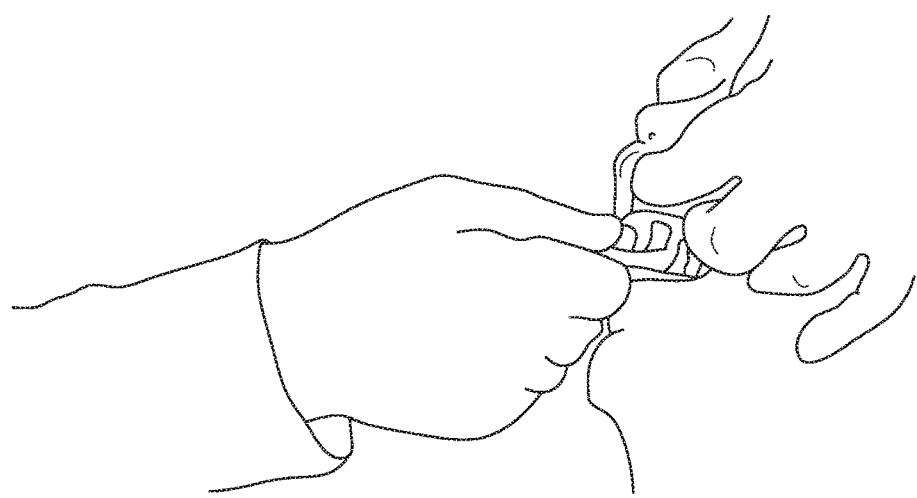
FIG. 8B illustrates a base impression being taken.
Figure 9:
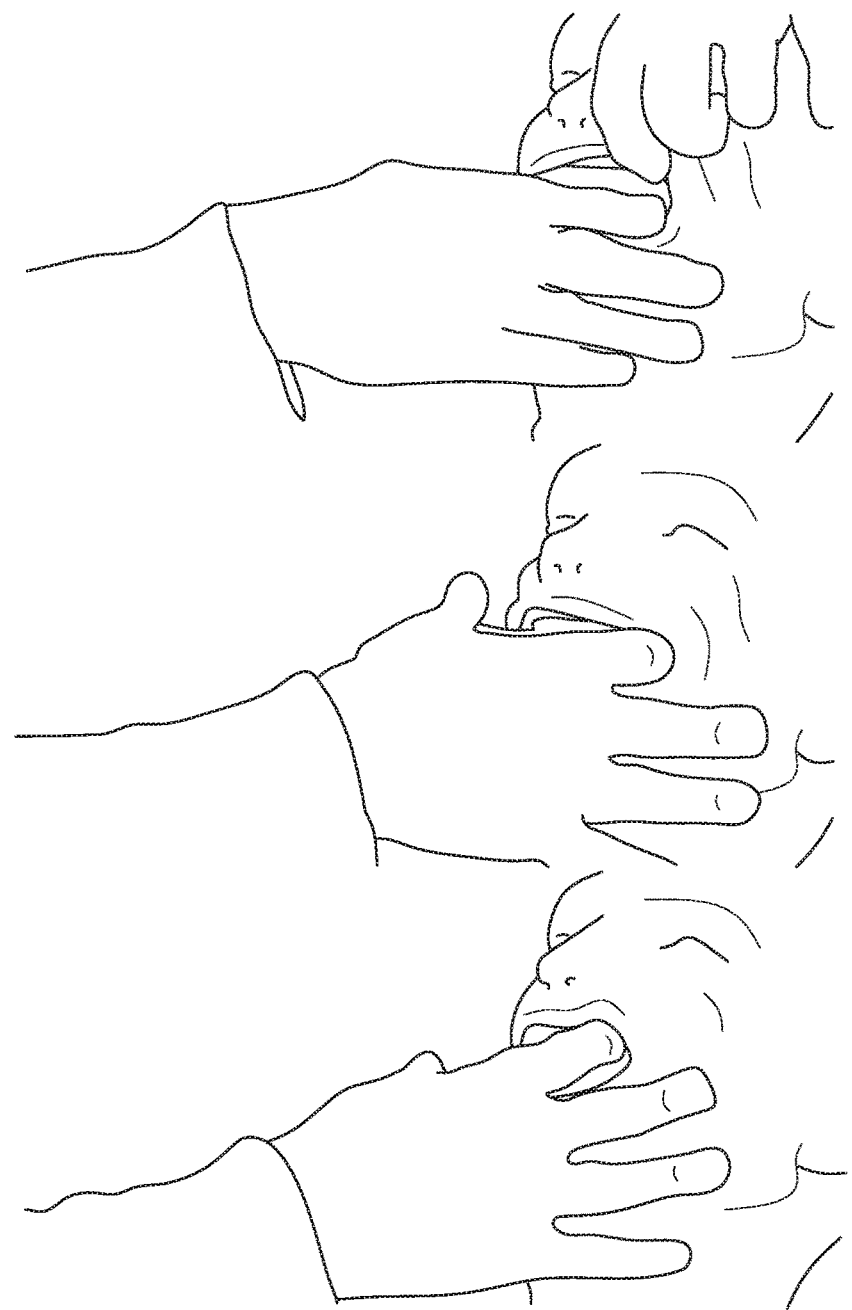
FIG. 9 illustrates the use of a finger to properly push base impression putty into the upper left buccal vestibule of a patient.

Once the impression tray has been loaded with impression putty, insert the loaded tray into the patient's mouth as soon thereafter as possible to reduce putty setting prior to placement. Place the loaded tray only slightly onto the patients teeth (as shown in FIG. 8A). Then grasp the impression tray handle with the fingers of one hand while grasping the patient's lip with the other hand (illustrated in FIG. 8B). Ensure that the impression tray has been properly positioned on the teeth then pull the patient's lip out and over the impression and have the patient bite down fully through the putty until the teeth hit the impression tray (shown in FIG. 8B). Instruct the patient to stay closed gently, and then push the putty fully into the vestibule of the patient's buccal corridors around all of the molars and bicuspids. In some embodiments, a finger can be used (as shown in FIG. 9): a finger can be inserted into the patient's left buccal corridor (to the back molars first) and used to push the putty fully into the vestibule for all molars and bicuspids. In other embodiments, a tool may be used to push the putty fully into the vestibule for all molars and bicuspids: any mechanism may be used which is capable of fully and appropriately pushing the putty into the vestibule for all molars and bicuspids. Push the putty fully into the vestibule for all molars and bicuspids in the patient's right and left buccal corridors (shown in FIGS. 9 and 10). After all molars and bicuspids have been addressed, pull out the patient's lip and push putty in the anterior fully into the vestibule. As addressed above, in some embodiments, a finger can be used to push the putty into the vestibule (illustrated in FIG. 11). Alternatively, in some embodiments, a tool may be used to push the putty into the vestibule: any mechanism may be used which is capable of fully and appropriately pushing the putty into the vestibule.

Figure 12A:
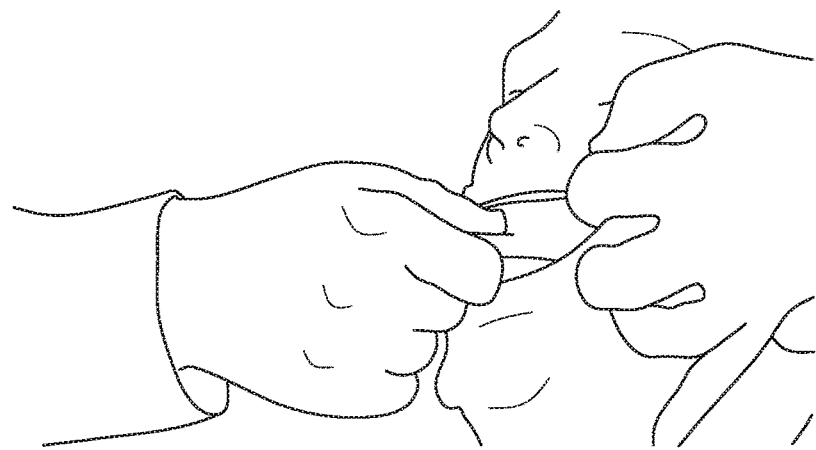
FIG. 12A illustrates a set, or partially set, impression being loosened.

To ease removal of the impression once it has hardened sufficiently, it may be useful to loosen the impression (before it has fully set) as if it was being removed then have the patient bite the impression back into place (shown in FIG. 12A). In some embodiments, the impression is lifted off only once, twice or more, three times or more, four times or more, or more than five times consecutively. In some embodiments, the impression may not require lifting off at all.

Figure 12B:
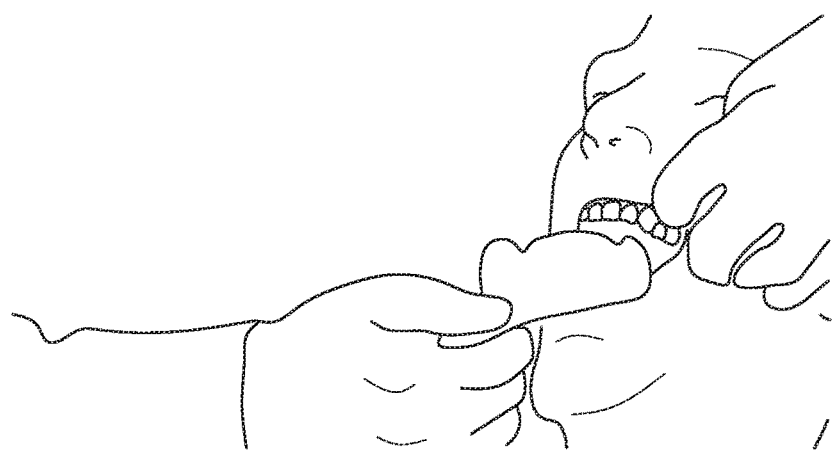
FIG. 12B illustrates the removal of an appropriately set impression.
Figure 13A:
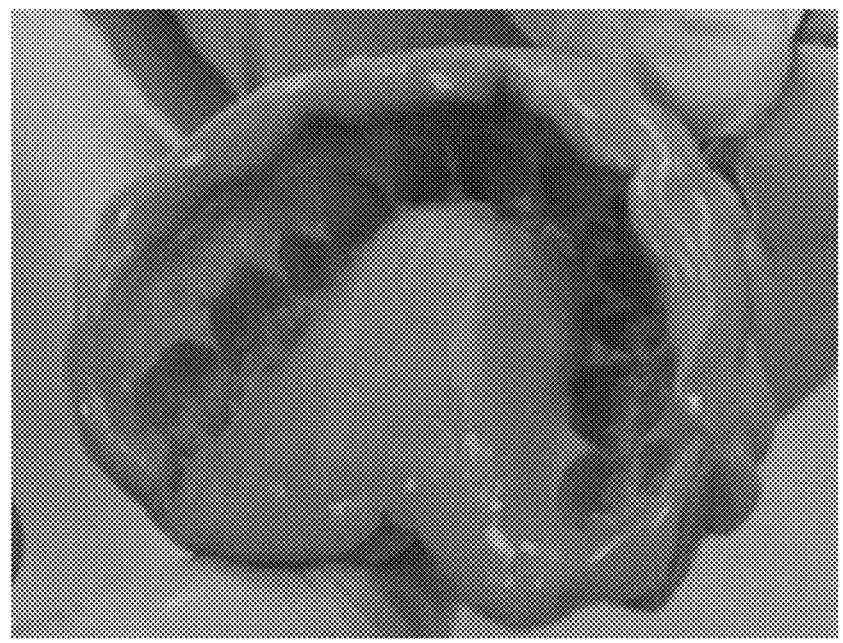
FIGS. 13A-13B illustrate successfully removed and set base impressions taken using impression putty.
Figure 13B:
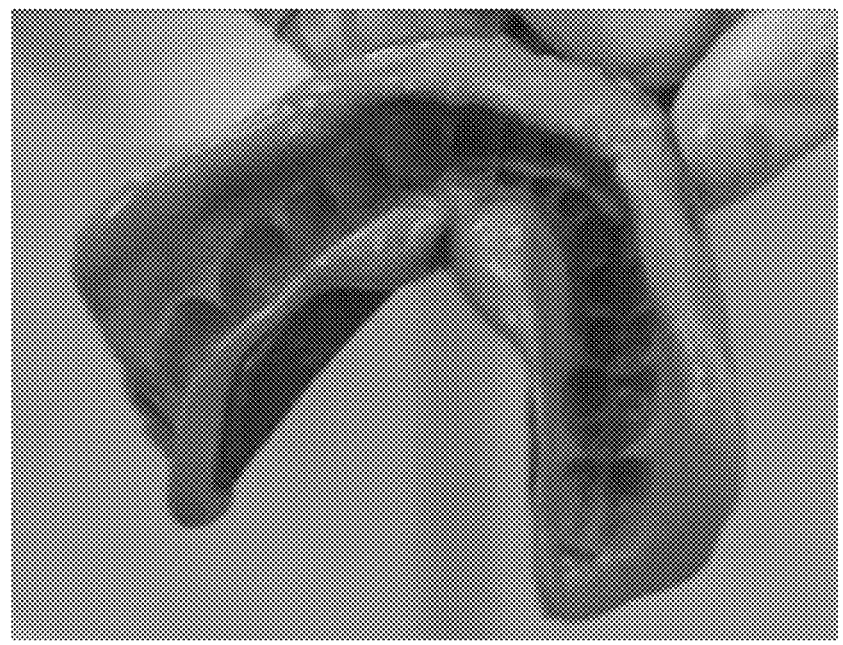

FIG. 12B illustrates the removal of a set impression. As soon as the putty has begun to set, the impression may be removed from the patient's mouth. In some embodiments, the level of set may be tested by pushing on the putty with a fingernail: when the putty rebounds upon pressure applied with a fingernail, the putty has begun setting. The putty can then be allowed to set fully after removal from the mouth. In some embodiments, the impression may be left in the mouth until fully set prior to removal. FIGS. 13A and 13B illustrate successfully removed and set base impressions with FIG. 13A being a base impression of a patient's upper teeth and FIG. 13B being a base impression of a patient's lower teeth. After removal, the impressions can be observed to confirm that the putty impression was fully seated and that putty extends into the facial and lingual vestibules past the gingival margin area and around the entire arch (facial, lingual, anterior & posterior). In some embodiments, the putty extends into the facial and lingual vestibules in the range of about 2-15 mm, about 3-13 mm, about 5-11 mm, about 6-9 mm, and about 7-8 mm, including about 5-10 mm.

In some embodiments, a small amount of putty may be added to locations of the base impression where the putty did not extend past all teeth and fully into the vestibule. In embodiments in which putty 702 is added to any of the vestibular extension areas, a bur can be used to first remove all the interproximals in the putty impression, thereby advantageously making it easier to re-seat the impression in the patient's mouth. To add putty to the impression, the first base impression can be cleaned around any areas to which putty material will be added (e.g., with alcohol or any other such cleaner) and then dried. As mentioned before, if there is any exposed polycarbonate, tray adhesive may be applied and dried to encourage bonding between the putty and the tray. Putty can be applied where needed then the impression re-inserted into the patient's mouth. After the patient bites down fully again, the newly applied putty, if applied properly, can fill the prior void thereby finishing the base impression. The finished base impression can be removed from the patient's mouth once the putty material is fully set. In other embodiments, the impression can be removed after the impression material has begun setting, but prior to being fully set, and allowed to finish setting outside the mouth.

Taking the Base Impression Using KöR® Heavy Body

Figure 14:
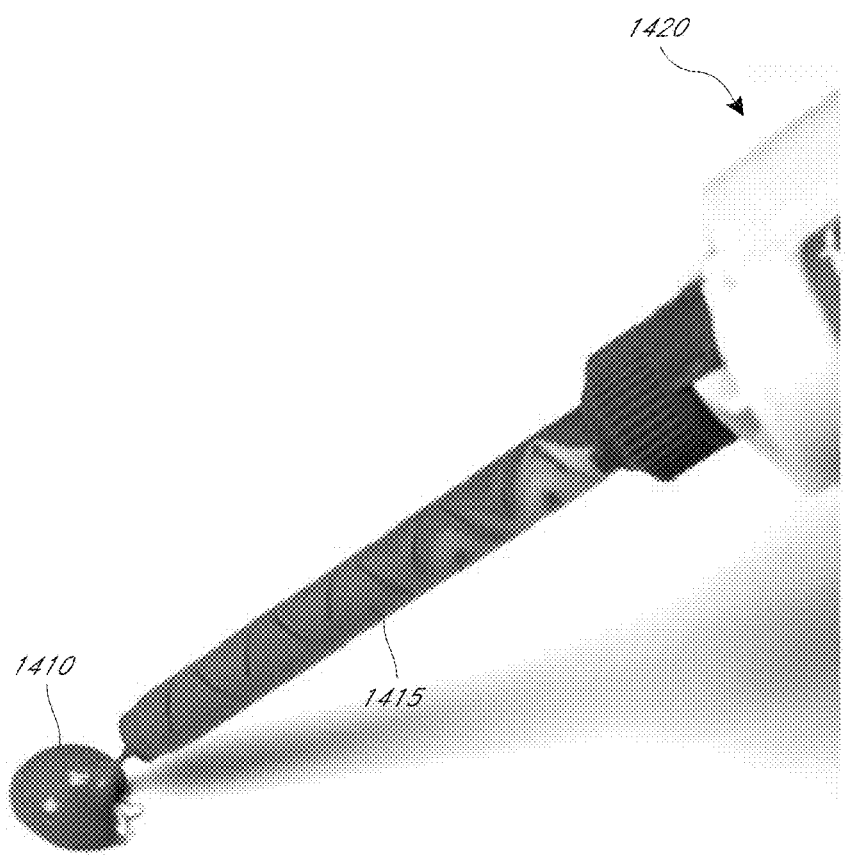
FIG. 14 illustrates heavy body impression material being mixed and extruded from the tip of a mixing cannula.

When using KöR® Heavy Body (or another heavy body impression material) for the base material, load a KöR® Heavy Body impression material cartridge 1420 (or any other heavy body impression material) into a standard dispensing gun (not shown). The KöR® Heavy Body can be used as indicated by the manufacturer. In some embodiments, the KöR® Heavy Body can be loaded into a standard dispensing gun with the automix heavy body cartridge and a large mixing cannula 1415. In some embodiments, a small amount of the impression material 1410 is extruded from the tip of the large mixing cannula 1415 and discarded (as shown in FIG. 14).

Figure 15A:
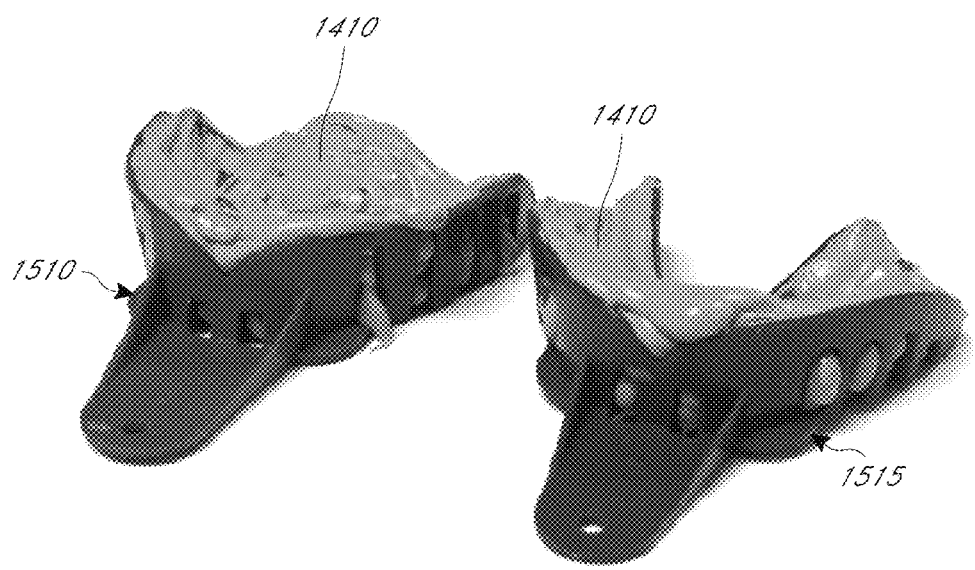
FIGS. 15A-15B illustrate impression trays, such as those shown in FIGS. 1A-1F, properly filled with heavy body impression material, such as that shown in FIG. 14.
Figure 15B:
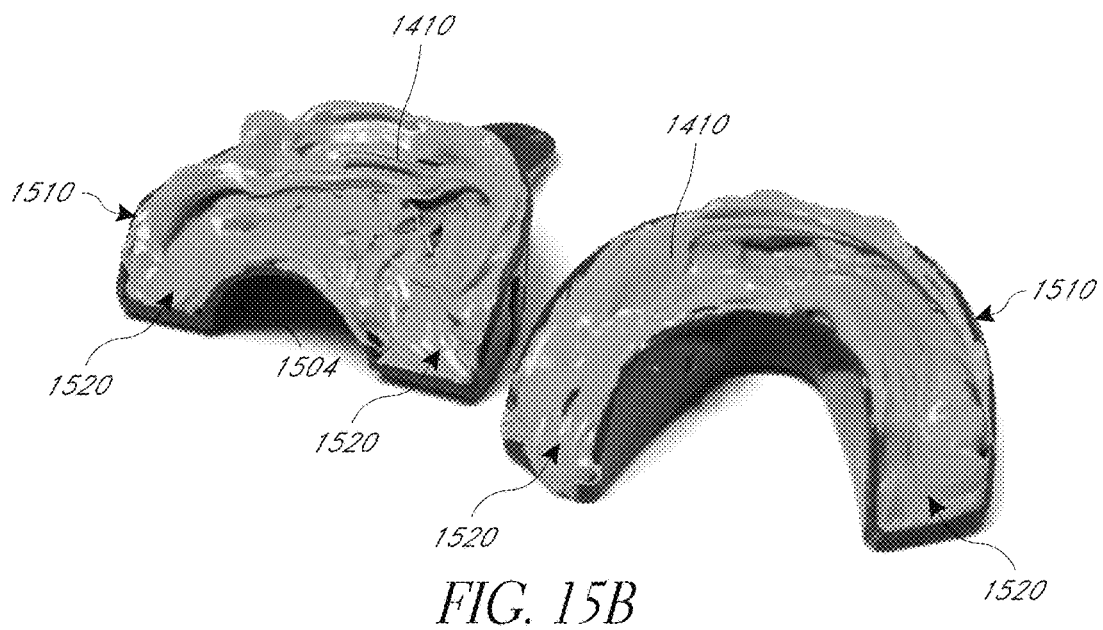

Load or fill the impression trays with the impression material 1410. FIGS. 15A and 15B illustrate properly filled upper trays 1510 and lower trays 1515 from the front and rear respectively. Load sufficient impression material 1410 in the trays to ensure a full and complete impression. In some embodiments, the upper tray 1510 and the lower tray 1515 are filled up to the edges of the trays. In some embodiments, the palate portion 1504 of the upper tray 1510 is slightly covered with the impression material 1410 (shown in FIG. 15B). In some embodiments the molar area 1520 is completely filled with impression material 1410. In some embodiments, the palate portion 1504 of the upper tray 1510 is not fully covered with impression material 1410 (not shown). In other embodiments, the palate portion 1504 of the upper tray 1510 is completely filled with impression material 1410 (not shown).

Figure 16A:
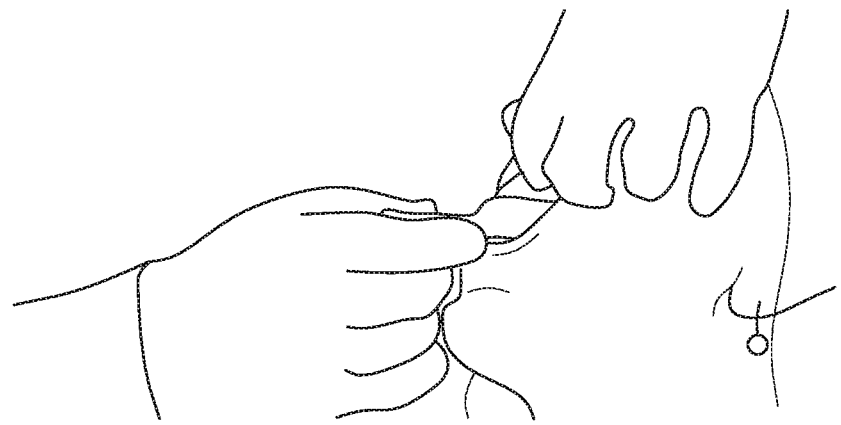
FIGS. 16A-16C illustrate a method of taking a base impression using impression trays and heavy body impression material, such as those shown in FIGS. 15A-15B.
Figure 16B:
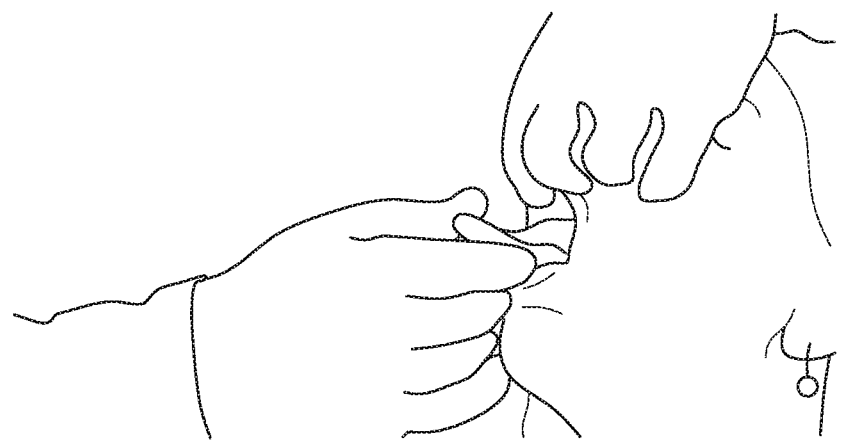
Figure 16C:
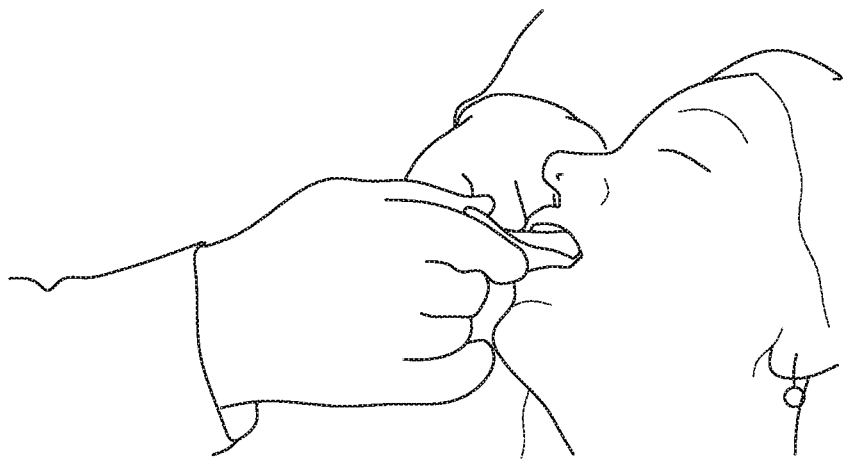

Once the impression tray has been loaded with impression material, insert the loaded tray into the patient's mouth and place the loaded tray only slightly onto the patients teeth (as shown in FIG. 16A). Then grasp the impression tray handle with the fingers of one hand while grasping the patient's lip with the other hand (illustrated in FIG. 16B). Ensure that the impression tray has been properly positioned on the teeth then pull the patient's lip out and over the impression (shown in FIG. 16B) and have the patient bite down fully through the impression material until the teeth hit the impression tray (shown in FIG. 16C). The handle of the impression tray can be held while the patient bites down so that the patient advantageously does not push it partially out of the mouth when biting down (shown in FIG. 16C).

Figure 17:
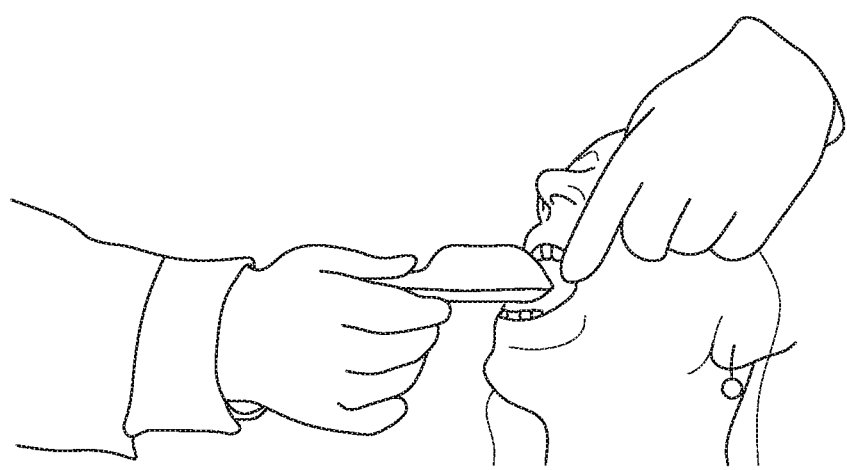
FIG. 17 illustrates the removal of a base impression taken using impression trays and heavy body impression material, such as those shown in FIGS. 15A-15B.
Figure 18A:
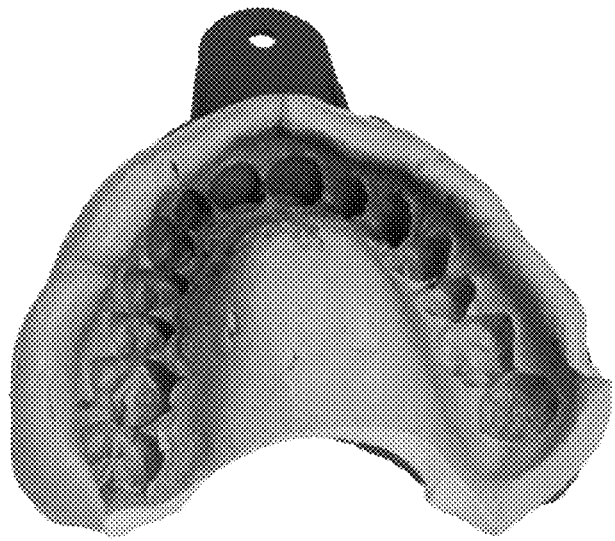
FIGS. 18A-18B illustrate successfully removed and set base impressions taken using heavy body impression material.
Figure 18B:
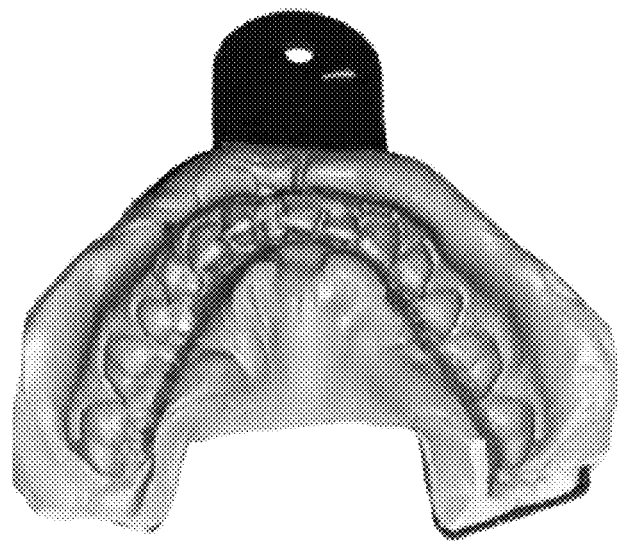

FIG. 17 illustrates the removal of a set impression. As soon as the heavy body impression material has begun to set, the impression may be removed from the patient's mouth. In some embodiments, the degree/level of set may be tested by pushing on the heavy body impression material with a fingernail: when the heavy body impression material rebounds upon pressure applied with a fingernail, the heavy body impression material has begun setting. The heavy body impression material can then be allowed to set fully after removal from the mouth. In some embodiments, the heavy body impression material can be fully set prior to removal from the mouth. FIGS. 18A and 18B illustrate successfully removed and set heavy body impression material base impressions with FIG. 18A being a base impression of a patient's upper teeth and FIG. 18B being a base impression of a patient's lower teeth. After removal, the impressions can be observed to confirm that the impression was fully seated and that heavy body impression material extends into the facial and lingual vestibules past the gingival margin area and around the entire arch (facial, lingual, anterior & posterior). In some embodiments, the heavy body impression material extends into the facial and lingual vestibules in the range of about 2-15 mm, about 3-13 mm, about 5-11 mm, about 6-9 mm, and about 7-8 mm, including about 5-10 mm. The impressions in FIGS. 18A and 18B illustrate proper impressions in which the tray was fully seated and the heavy body impression material extends into the facial and lingual vestibules in the range of about 5-10 mm past the gingival margin area around the entire arch (facial, lingual, anterior & posterior).

As discussed with respect to the creation of impression putty base impressions, in some embodiments, a small amount of KöR® Heavy Body impression material may be added to locations of the base impression if the impression material did not extend past all teeth and fully into the vestibule. In such embodiments adding to any of the vestibular extension areas, a bur can be used to first remove interproximals in the heavy body base impression, thereby advantageously rendering it easier to re-seat the impression in the patient's mouth. To add impression material, the first base impression can be cleaned around any areas to which impression material will be added (e.g., with alcohol or any other such cleaner) and then dried. As already mentioned, if there is any exposed polycarbonate, tray adhesive may be applied to encourage bonding between the impression material and the tray. Heavy body impression material can be applied as needed then the impression re-inserted into the patient's mouth. After the patient bites down fully again, the newly applied impression material, if applied properly, can fill the prior void thereby finishing the base impression. The finished base impression can be removed from the patient's mouth once the newly added impression material is fully set. In other embodiments, the impression can be removed after the impression material has begun setting, but prior to being fully set, and allowed to finish setting outside the mouth.

Preparing the Base Impressions for the Wash Impressions

After taking a successful base impression, using either an impression putty or a heavy body impression material—or any other appropriate material, it can be seen that the base impressions can have numerous irregularities (e.g., spikes and folds) created by embrasures, occlusal grooves, etc. Such irregularities can be observed in FIGS. 13A, 13B, 18A, and 18B. In some embodiments, irregularities can be ground out and smoothed internally to advantageously improve the quality of the wash impression. In embodiments in which the internal surfaces of the base impression are smoothed and ground, all spikes and folds (any irregularities) are removed. In some embodiments, the gingival margin areas and the area of attached gingiva can be slightly relieved in the range of about 0.1-1.0 mm deep, about 0.2-0.9 mm deep, about 0.3-0.8 mm deep, and about 0.4-0.7 mm deep, including about 0.5 mm deep or any other depth which appropriately prepares the aforementioned surfaces. In some embodiments, the facial and lingual tooth areas can be relieved in the range of about 0.1-1.0 mm deep, about 0.2-0.9 mm deep, about 0.3-0.8 mm deep, and about 0.4-0.7 mm deep, including about 0.5 mm deep or any other depth which appropriately prepares the aforementioned surfaces. In some embodiments, the occlusal surfaces of bicuspids and molars can be relieved, leaving only imprints of cusp tips and incisal edges visible. In some embodiments, the impression material apical to the attached gingiva is left intact (not ground down) to advantageously aid in sealing the impression during the wash impression and creating the appropriate hydraulic pressure for the wash impression.

Figure 19A:
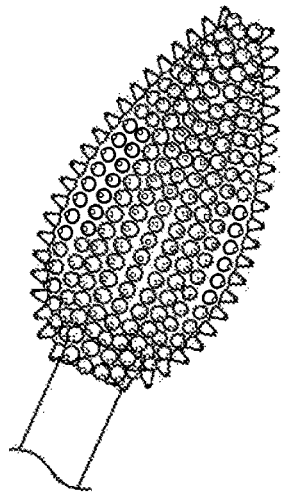
FIGS. 19A-19D illustrate various shapes and sizes of burs.
Figure 19B:
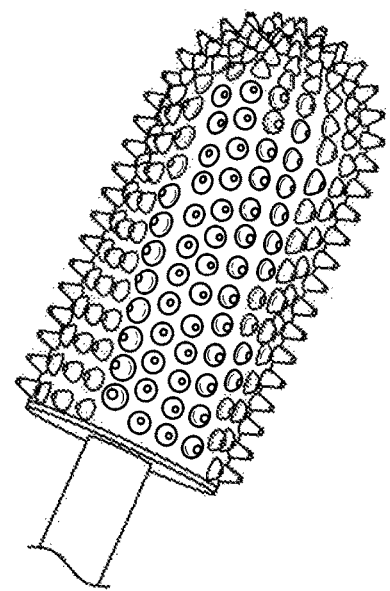
Figure 19C:
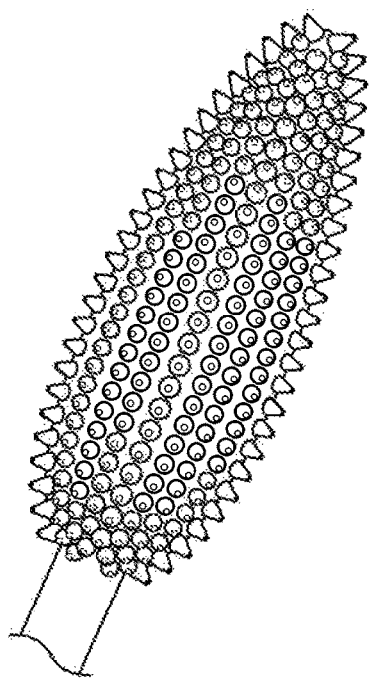
Figure 19D:
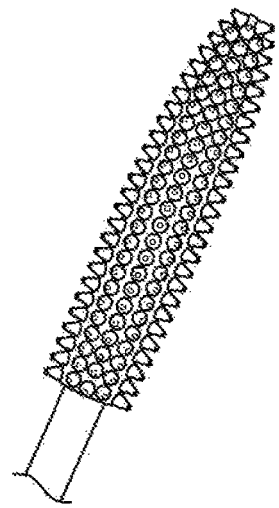
Figure 20A:
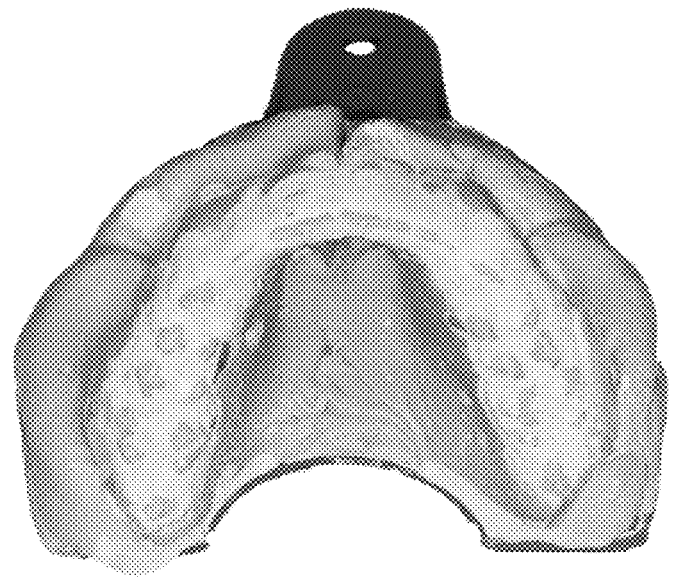
FIGS. 20A-20B illustrate base impressions, such as those shown in FIGS. 13A-13B and 18A-18B, that have been prepared for taking a wash impression.
Figure 20B:
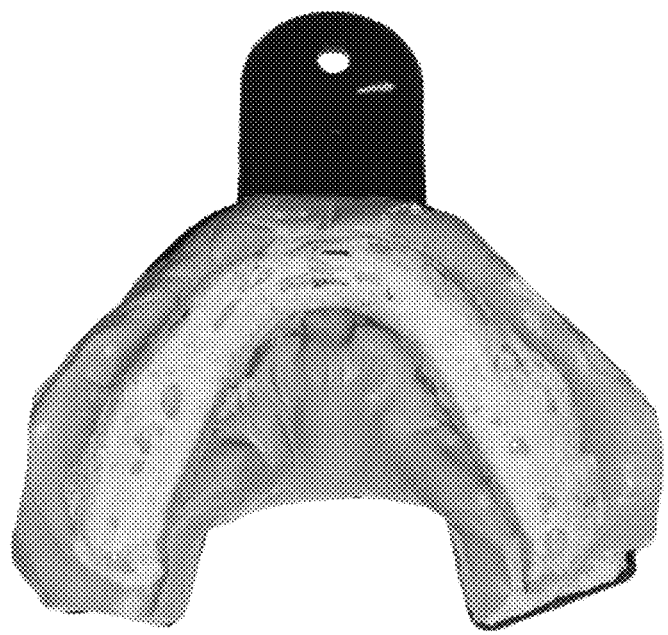
Figure 21:
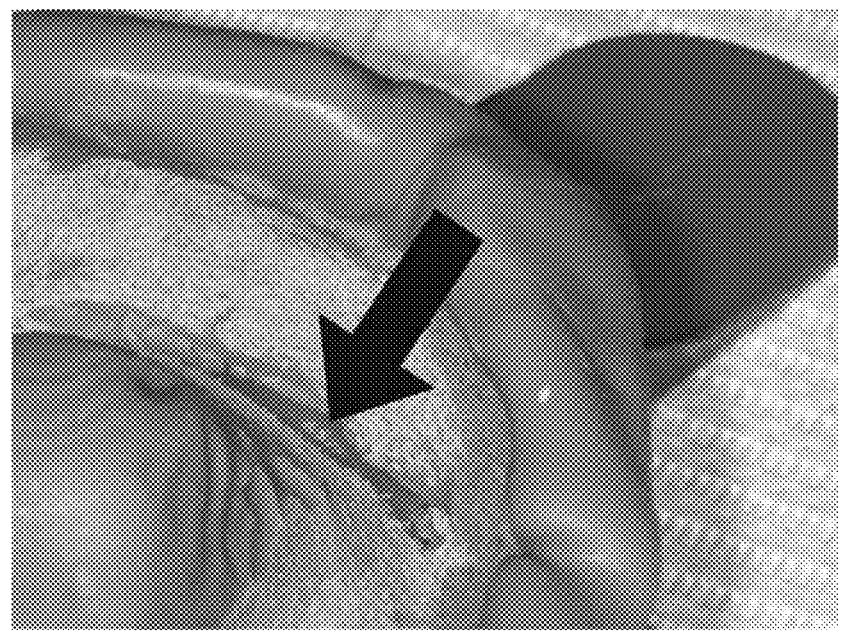
FIG. 21 illustrates a base impression prepared for taking a wash impression in which some of the impression tray has been exposed.

In embodiments in which grinding of the base impression is desired, the following sequence can be followed. A pear-shaped bur (illustrated in FIG. 19A), or any other appropriately shaped bur, can be used to remove the bulk of the interproximal spikes and on the gingival margin areas to remove approximately 0.5 mm depth (or any other depth as disclosed above) of the gingival margins and the area just apical to the gingival margin areas (areas of attached gingiva). Next, a bull nose shaped bur (illustrated in FIG. 19B), or any other appropriately shaped bur, can be used in the molar areas and the bicuspid areas to finish removal of interproximal spikes and to remove approximately 0.5 mm depth (or any other depth as disclosed above) of the base impression from the facial and lingual tooth surface areas. The same bull nose bur can be used to flatten the occlusal surfaces of the bicuspids and molars, leaving only the imprints of the cusp tips. Then, a flame shape bur, (illustrated in FIG. 19C), or any other appropriately shaped bur, can be used in the upper anterior areas to finish removal of interproximal spikes and to remove approximately 0.5 mm depth (or any other depth as disclosed above) of base impression from the facial and lingual tooth surface areas. Finally, a narrow shape bur (illustrated in FIG. 19D), or any other appropriately shaped bur, can be used in the narrow lower anterior areas to finish removal of interproximal spikes and to remove approximately 0.5 mm depth (or any other depth as disclosed above) of base impression from the facial and lingual tooth surface areas. After using the burs to grind out base impression material, any debris left inside the impression from use of the burs can be removed using a strong air spray or another appropriate mechanism. The base impressions can then be wiped out with dry gauze and/or dry cotton tipped swabs. FIGS. 20A and 20B illustrate a properly ground out upper jaw base impression, and a properly ground out lower jaw base impression, respectively. After grinding out the base impression as disclosed herein, if there is any polycarbonate exposed (as shown in FIG. 21, denoted by the heavy black arrow) tray adhesive can be applied to the exposed polycarbonate and let dry to advantageously improve and enhance adhesion of the wash impression to the tray/base impression.

Figure 22A:
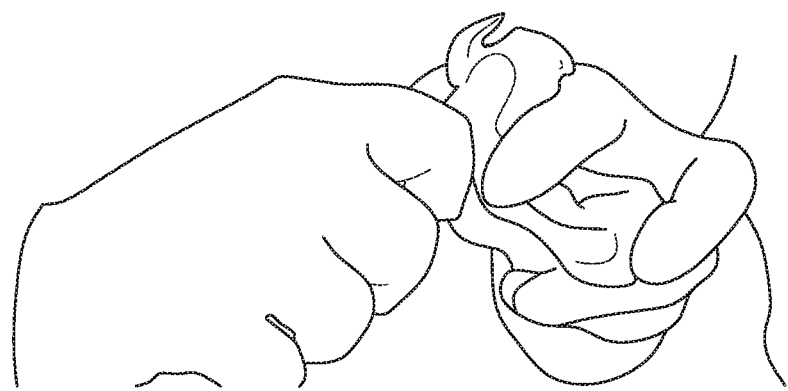
FIGS. 22A-22B illustrates additional preparation of a base impression for taking a wash impression.
Figure 22B:
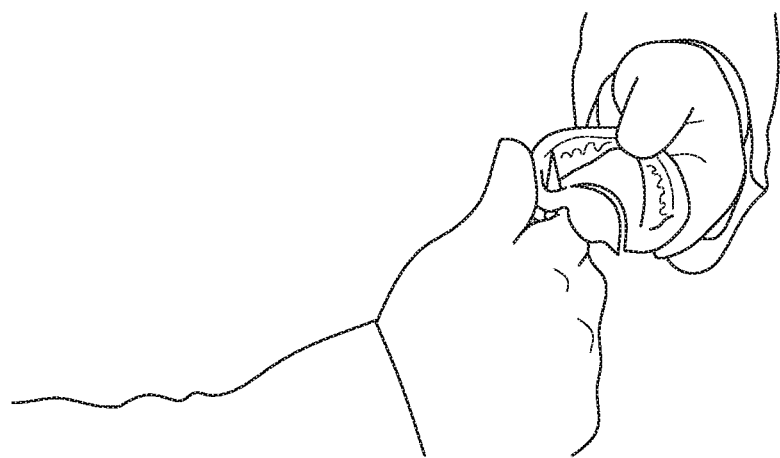

When taking the base impression and seating the base impression in the patient's mouth, impression material or impression putty may squish laterally over the buccal flanges of the tray into the buccal corridor. Excess putty or heavy body extending laterally into the buccal area can make it difficult to re-insert the impression back into the patient's mouth for the wash impression. Therefore, in some embodiments, the excess putty or heavy body which has extended laterally to the tray in the buccal areas may be trimmed off using a sharp knife or blade or any other appropriate mechanism. Removal of excess putty on a base impression as just disclosed is shown in FIG. 22A. In some embodiments, care is taken not to remove the vestibular extensions. Excess putty or heavy body extending posteriorly into the soft palate area may tend to gag the patient upon reinsertion of the impression back into the patient's mouth for the wash impression. Therefore, in some embodiments, the excess putty or heavy body which has extended posteriorly into the soft palate (an over-extension of the base impression) area may be trimmed off using a sharp knife or blade or any other appropriate mechanism. Removal of excess heavy body on a base impression as just disclosed is shown in FIG. 22B.

Prior to taking the wash impression any impression material that has not been ground with a bur can be cleaned by wiping with alcohol soaked gauze and let dry. In some embodiments, the alcohol can be air dried (i.e., allowed to evaporate). In other embodiments, the alcohol can be dried with an air syringe thereby advantageously decreasing the time required for full drying.

Taking the Light Body Wash Impression

Figure 23:
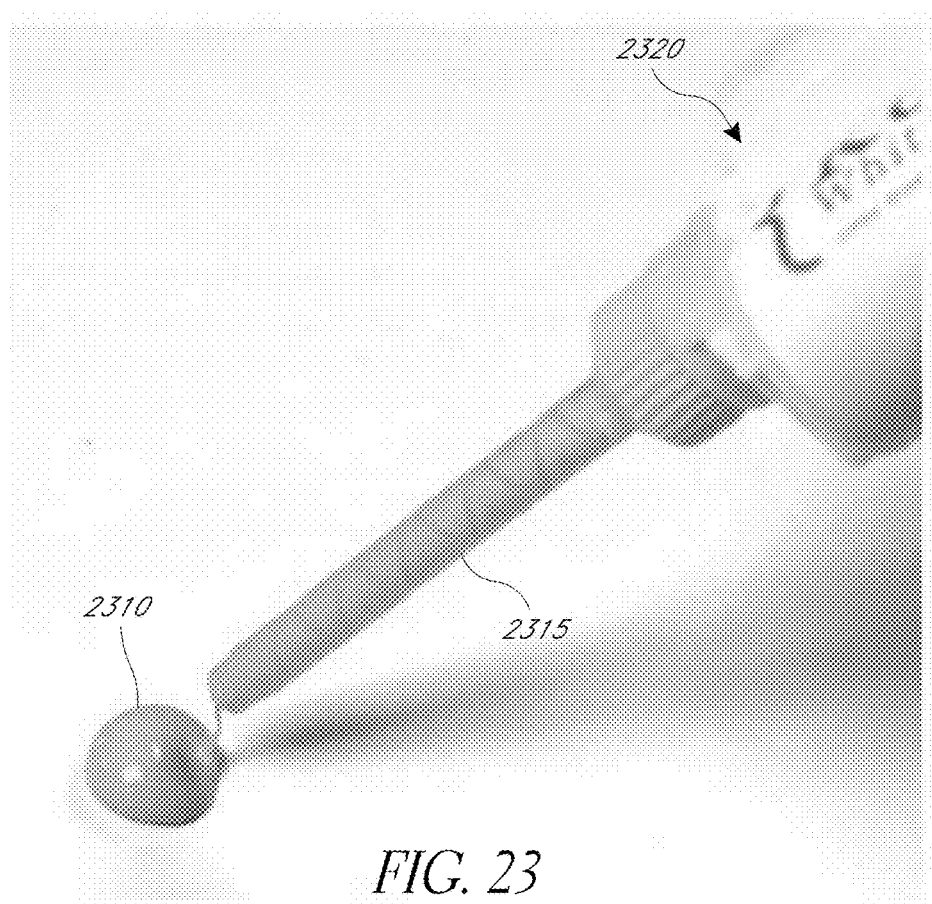
FIG. 23 illustrates wash impression material being mixed and extruded from the tip of a mixing cannula.

When using KöR® Light Body (or another light body impression material), load a KöR® Light Body impression material cartridge 2320 (or any other light body impression material) into a standard dispensing gun (not shown). The KöR® Light Body can be used as indicated by the manufacturer. In some embodiments, the KöR® Light Body can be loaded into a standard dispensing gun with an automix cartridge and a medium sized mixing cannula 2315. In some embodiments, a small amount of the light body wash impression material 2310 is extruded from the tip of the medium sized mixing cannula 2315 and discarded (as shown in FIG. 23).

Figure 24A:
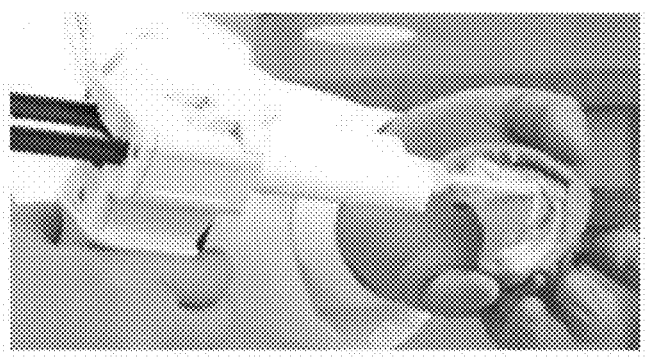
FIGS. 24A-24D illustrate a prepared base impression being filled with wash impression material.
Figure 24B:
Figure 24C:
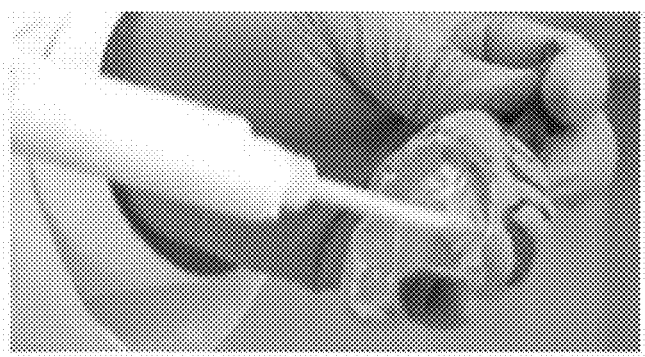
Figure 24D:
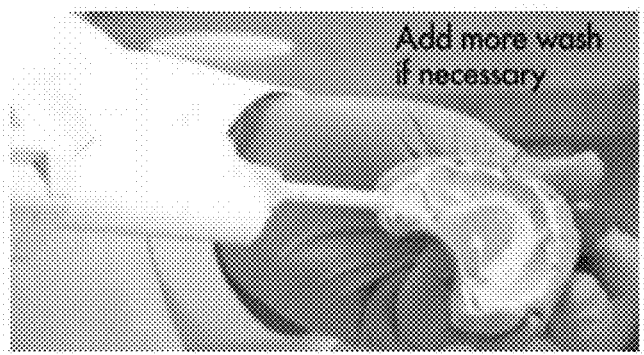

Load or fill the base impression with the light body wash impression material 2310 as illustrated in FIG. 24A, slightly over-filling tooth areas inside the base impression. In some embodiments, the light body wash impression material 2310 is pushed all the way up onto the walls of the base impression, fully up to the edges of the vestibular extensions (shown in FIG. 24B), up onto some of the palate (shown in FIG. 24C), and posteriorly past the molar areas (shown in FIG. 24D). In some embodiments, excess light body wash impression material 2310 is added to the base impression to advantageously ensure that sufficient hydraulic pressure is created thereby ensuring the best impression possible.

Figure 25A:
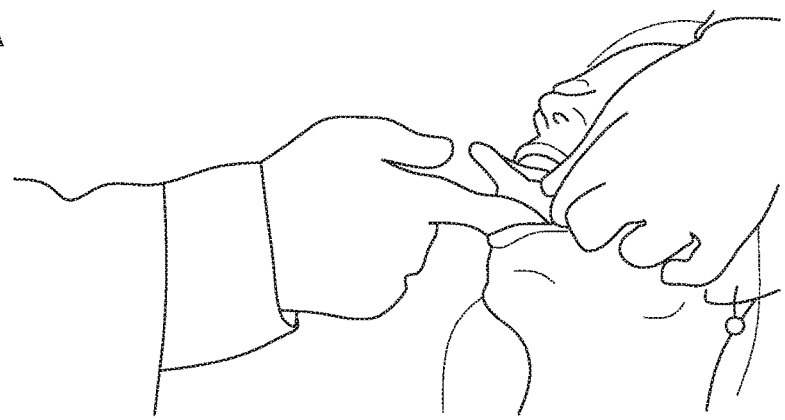
FIGS. 25A-25C illustrate a method of taking a wash impression.
Figure 25B:
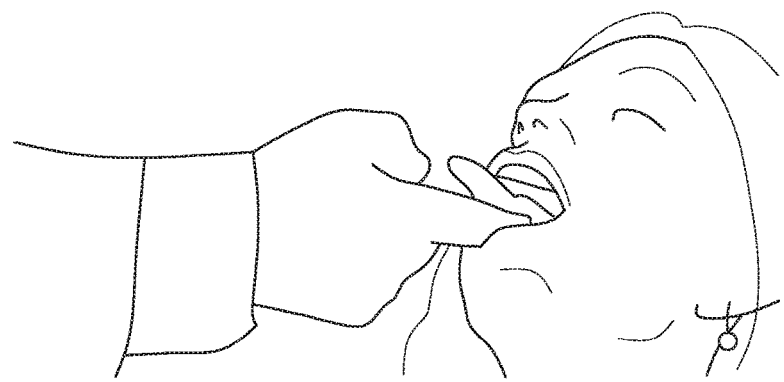
Figure 25C:
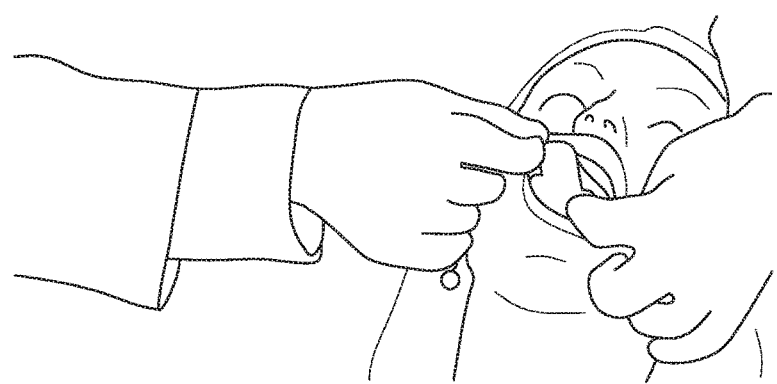

Once the base impression has been loaded with the light body wash impression material 2310, insert the loaded base impression into the patient's mouth and place the loaded base impression onto the teeth and compress the base impression onto the teeth. In some embodiments, the compression of the base impression with light body wash impression material 2310 is done using one rapid, forceful movement (shown in FIG. 25A). The one rapid, forceful movement may last for a duration in the range of about 0.5-3.5 seconds, about 1-3 seconds, and about 1.5-2.5 seconds, including about 2 seconds, or any other appropriate length of time capable of creating a wash impression. In some embodiments, the patient can create the rapid, forceful movement by biting the impression into place. The wash impression (base impression filled with light body wash impression material 2310) can then be held in place, with substantially no movement and substantially constant, mild pressure (shown in FIG. 25B) until the light body wash impression material 2310 has set. In some embodiments, the patient can hold the impression in place by biting on the impression. In some embodiments, after the wash material appears to be fully set, an additional time is waited before removing the impression because anterior teeth can be significantly cooler than body temperature which may increase the time required for the light body wash impression material 2310 touching those teeth to set. In these embodiments, the additional time waited is in the range of about 1 second-5 minutes, about 5 seconds-2.5 minutes, about 10 seconds-1 minute, and about 15-30 seconds, including about 20 seconds, or any other time which allows the light body wash impression material 2310 to fully set. If the patient's lip happens to be caught under the edge of the tray and needs to be released, the tray/base impression should not be released for any amount of time—rather, constant pressure must be applied for the entire time, even while freeing the caught lip (as shown in FIG. 25C). If pressure is released from the tray/base impression, the impression can tend to suck in air thereby creating bubbles in the wash impression, thereby damaging the wash impression and rendering it useless. When taking the lower jaw wash impression, the patient's swallowing may cause the patient's tongue to lift the impression slightly off the teeth (resulting in bubbles in the wash impression, thereby damaging the wash impression and rendering it useless). Therefore, in some embodiments, the patient can be instructed to refrain from swallowing until they have been told it is acceptable to resume (generally it is acceptable for the patient to resume swallowing after the light body wash impression material 2310 is mostly set).

If a wash impression finishes with bubbles or a void, the wash material can be ground out with the aforementioned burs and a new wash impression taken. Alternatively, the entire impression process may be re-started.

Pouring Impressions in the Completed Light Body Wash Impressions

Materials commercially available which can be used to take the light body wash impression tend to require de-gassing. In some embodiments, pouring an impression includes filling the impression with a casting material to create a model or cast of the impression (e.g., a patient's teeth and oral soft tissues). In some embodiments, the casting material is plaster. If impressions are poured too early in such an impression, it is likely that the resulting model (cast) will emerge with tiny bubbles coating the surface of the model. Therefore, in some embodiments, impressions are not poured before some time has elapsed after removal of the light body wash impression from the patient's mouth, including some time in the range of about 30 minutes-2 hours, and about 30 minutes-1.5 hours, including about 1 hour or any other time which allows the light body wash impression to fully de-gas.

Using the Hydraulic Pressure Dental Impression Technique for Crown, Bridge, Implant and Veneer Impressions When using the aforementioned technique for crown, bridge and veneer impressions, the aforementioned techniques can be supplemented with the following information.

When taking the base impression, any choice of gingival retraction method may be used if the margins of the tooth preparation or implant abutment are subgingival. After tooth preparations and retraction, the base impression can be taken. After the base impression has been taken, burs can be used around the tooth crown, veneer, onlay, etc. preparation areas in the impression as disclosed above; however, in addition to removing 0.5 mm (or any other appropriate depth as disclosed above) from the axial walls of the base impression, the entire occlusal or incisal surface can also be relieved in the range of about 0.1-1.0 mm deep, about 0.2-0.9 mm deep, about 0.3-0.8 mm deep, and about 0.4-0.7 mm deep, including about 0.5 mm deep or any other depth which appropriately prepares the aforementioned surfaces. Additionally, areas that extend between tooth preparations from facial to lingual can also be removed.

When taking the wash impressions, the light body wash impression material 2310 can be syringed around the preparations while the base impressions are filled with wash material, all being done immediately before, immediately after or at the same time as the retraction cord is being removed.

Theory Behind the Hydraulic Pressure Dental Impression Technique

The hydraulic pressure dental impression technique creates strong hydraulic pressure on the impression material against the teeth and gums, thereby advantageously resulting in an extremely detailed, accurate and reproducible impression. The technique involves an impression made of two layers of impression material, each layer being placed in a separate step as disclosed above.

Figure 26:
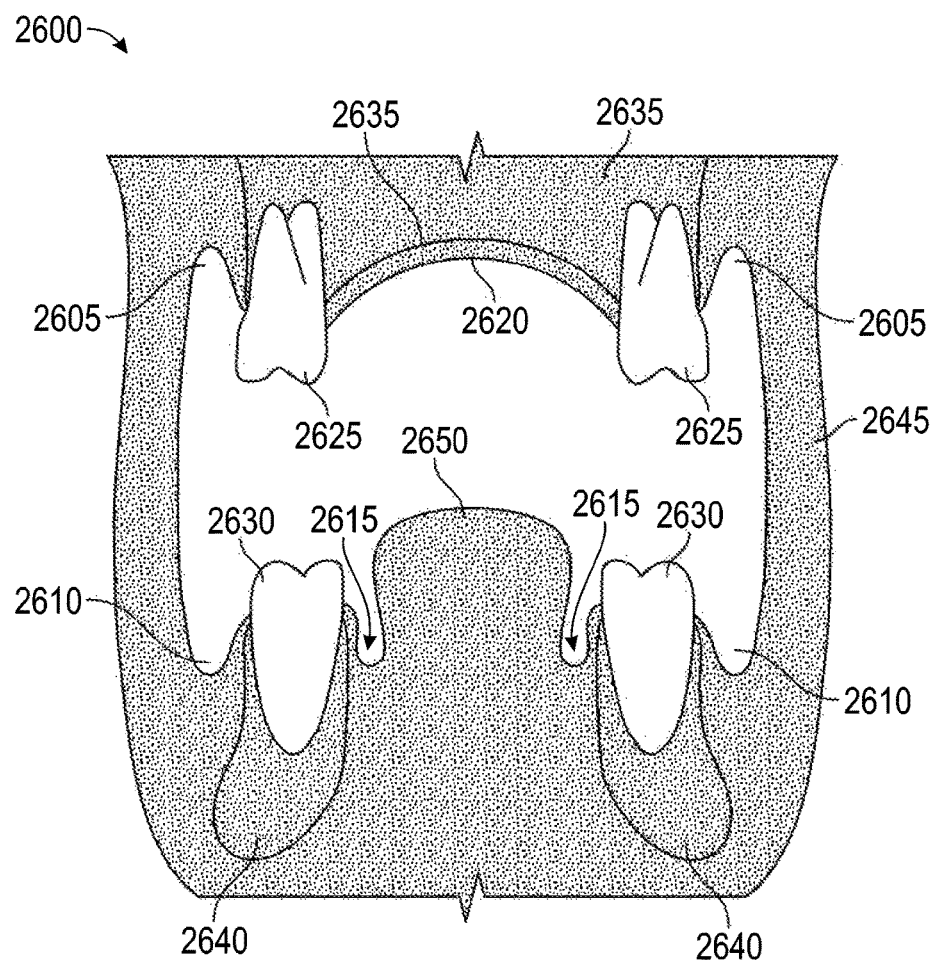
FIG. 26 illustrates a cross-sectional view of the human oral cavity.

The impression starts out with a "stock" impression tray as illustrated in FIG. 1. The first layer of the impression, sometimes referred to as the base impression, uses a thick impression material ("heavy body") or a putty consistency material ("impression putty"). The base impression forms to the teeth, gums, and vestibules creating a custom impression tray with which to take the second layer impression, sometimes referred to as the wash impression, which is taken using a lower viscosity light body wash impression material 2310. The light body wash impression material 2310 has hydraulic pressure placed on it during the hydraulic pressure dental impression technique process, thereby enabling it to be forced against the teeth and gums in an omni-directional fashion and to capture very fine detail. The base impression in this technique has certain characteristics which permit the creation of adequate hydraulic pressure when taking the final wash impression. In some embodiments, the base impression extensions into the vestibules seal the system for the wash impression which creates a closed system and omni-directional hydraulic pressure. FIG. 26 illustrates a cross-section of the human mouth 2600, including the upper buccal vestibules 2605, the lower buccal vestibules 2610, the lingual vestibules 2615, the palate 2620, upper molars 2625, lower molars 2630, upper jaw 2635, lower jaw 2640, the cheeks 2645, and the tongue 2650.

Figure 27A:
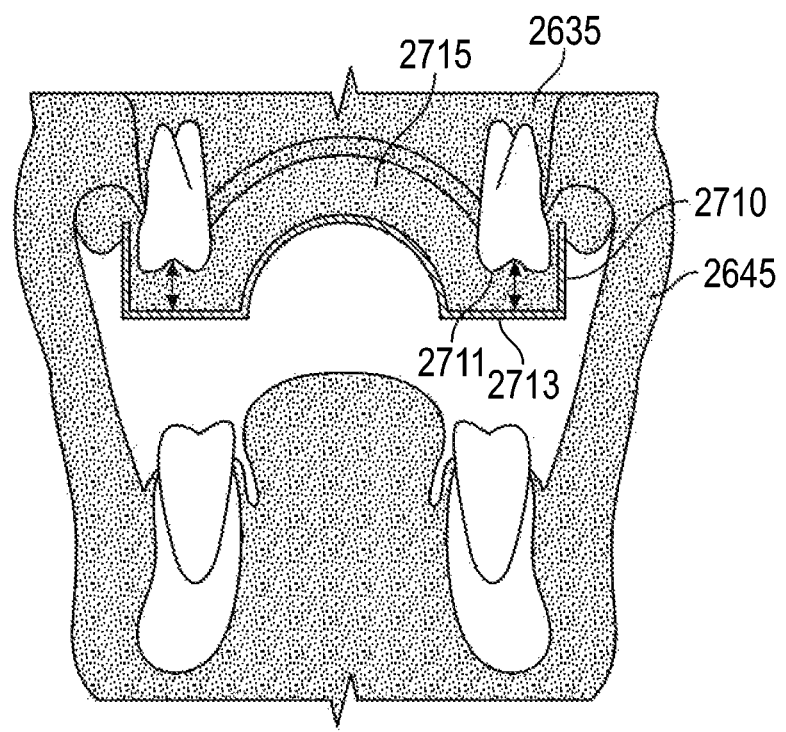
FIGS. 27A-27B illustrate cross-sectional views of conventionally placed impressions.
Figure 27B:
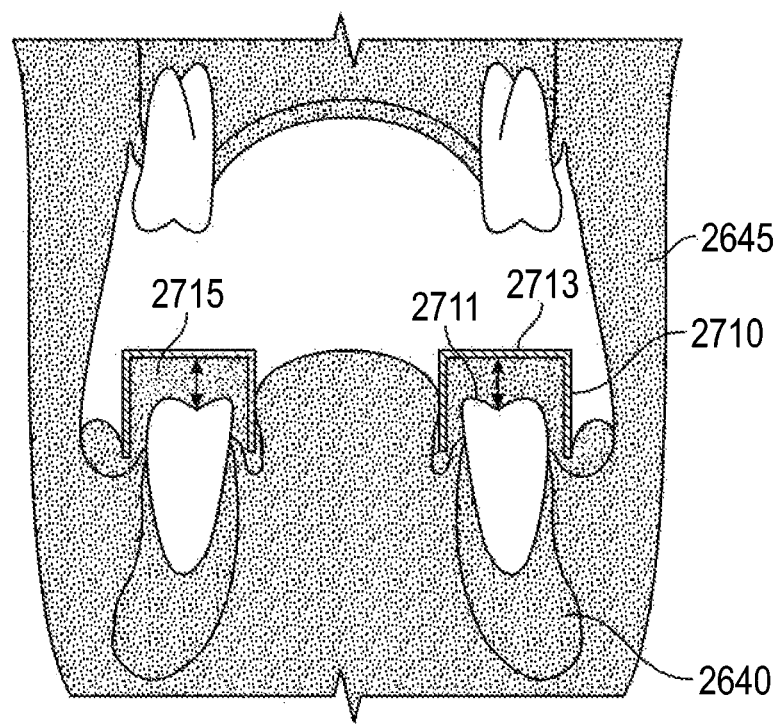
Figure 30A:
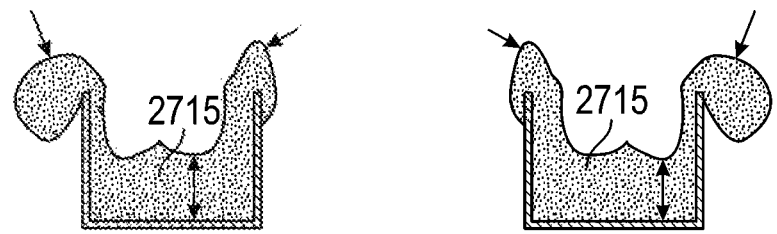
FIGS. 30A and 30C illustrate cross-sectional views of impressions taken using conventional impression techniques.
Figure 30B:
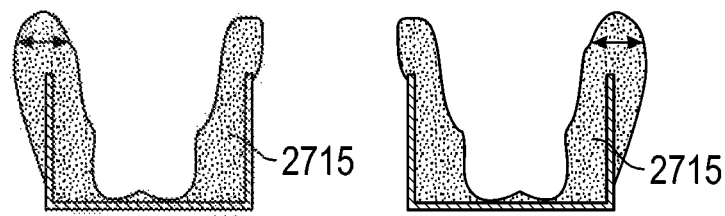
FIGS. 30B and 30D illustrate cross-sectional views of impressions taken using a method according to an embodiment of the present invention.
Figure 30C:
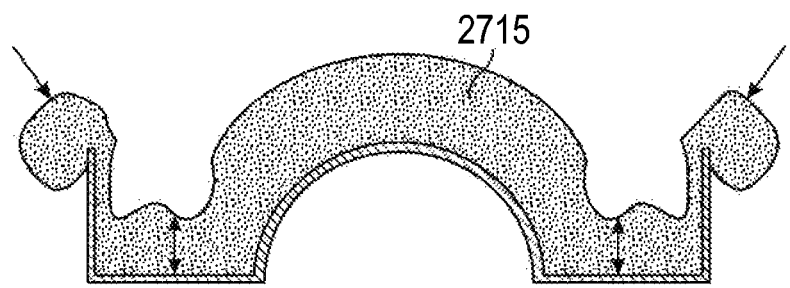
Figure 30D:
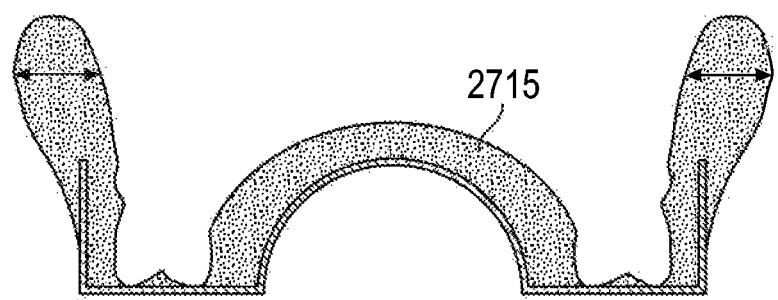

The conventional technique of taking a base impression includes the patient opening the mouth and the operator placing the stock impression tray filled with base impression material over the tops of the teeth then pushing the impression against the teeth with force. FIG. 27 illustrates a cross-section of the human mouth 2600 with conventionally placed base impressions, including a conventionally placed base impression 2710 on the upper jaw 2635 (FIG. 27A) and a conventionally placed base impression 2710 on the lower jaw 2640 (FIG. 27B). Because of the resistance of the base impression material 2715, the operator may not be able to seat the conventionally placed base impression 2710 fully (particularly when putty 702 is being used as the base impression material). The imperfect seating of the conventionally placed base impression 2710 and base impression material 2715 is illustrated in FIGS. 27A and 27B in which there is significant thickness of the base impression material, 2715 between the biting surface 2711 ("occlusal surface") of the upper molars 2625 and lower molars 2630 and the roof of the impression tray 2713 (denoted by the double ended arrows). FIGS. 30A and 30C illustrate the upper and lower, respectively, base impressions taken using a conventional technique: the thick depth of base impression material 2715 between the roof of the tray and the tooth surface can be easily seen (also denoted by double-ended arrows). Because stock trays are not fully seated onto the teeth, the sides of the stock impression trays do not extend deeply into the vestibules (shown in FIGS. 27A and 27B). Additionally, when the mouth is wide open, the cheeks 2645 stretch as shown in FIGS. 27A and 27B. When the cheeks 2645 are stretched, the vestibules tend to be pulled shallow, thereby preventing the impression material 2715 from going very deeply into the vestibules (including the upper buccal vestibules 2605, lower buccal vestibules 2610, and lingual vestibules 2615) (as illustrated in FIGS. 27A and 27B). FIGS. 30A and 30C illustrate how shallowly the base impression material 2715 enters the vestibules (including the upper buccal vestibules 2605 and the lower buccal vestibules 2610, and lingual vestibules 2615) (denoted by the heavy black arrows) when the cheeks 2645 are stretched.

Figure 28A:
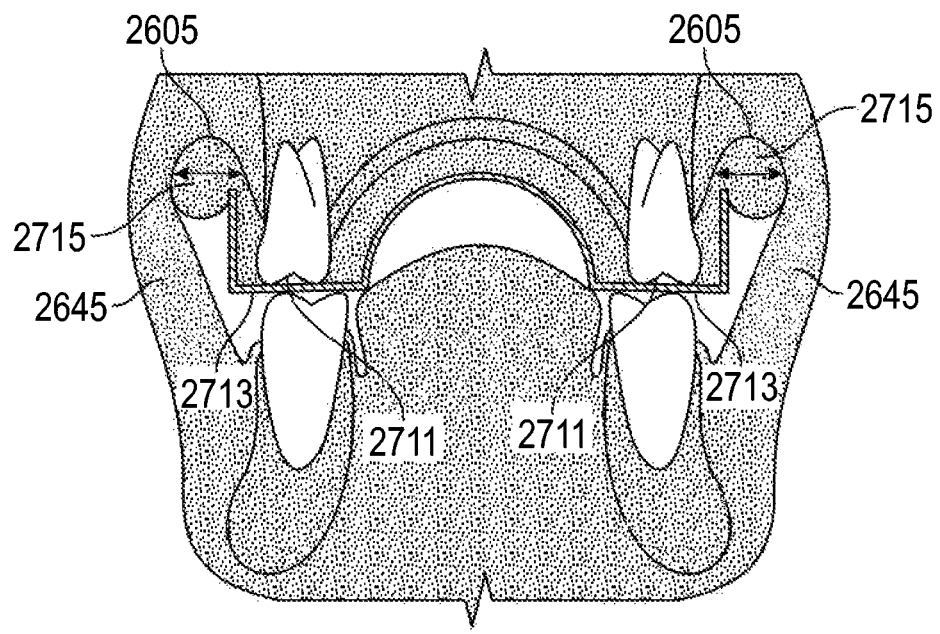
FIGS. 28A-28B illustrate cross-sectional views of impressions placed according to an embodiment of the present invention.
Figure 28B:
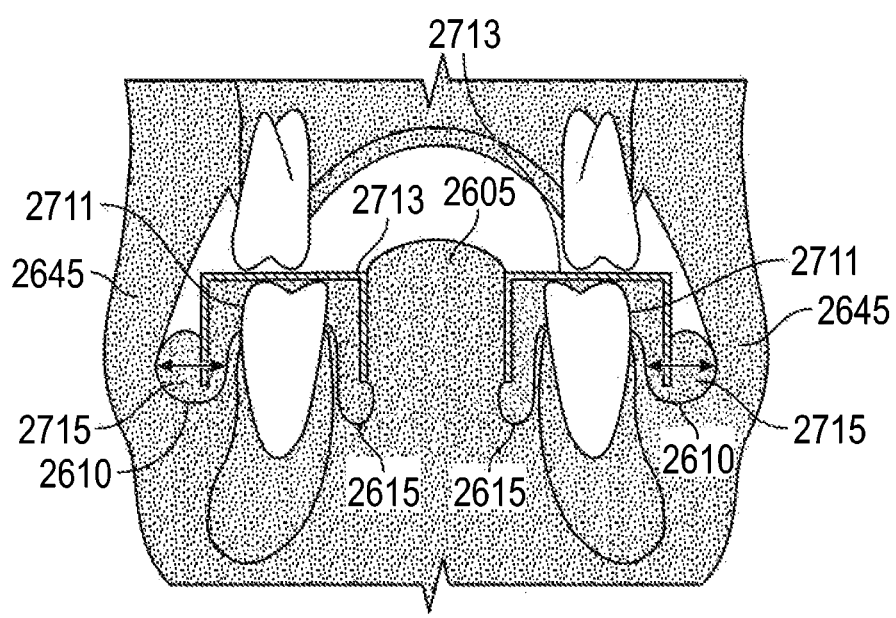
Figure 29A:
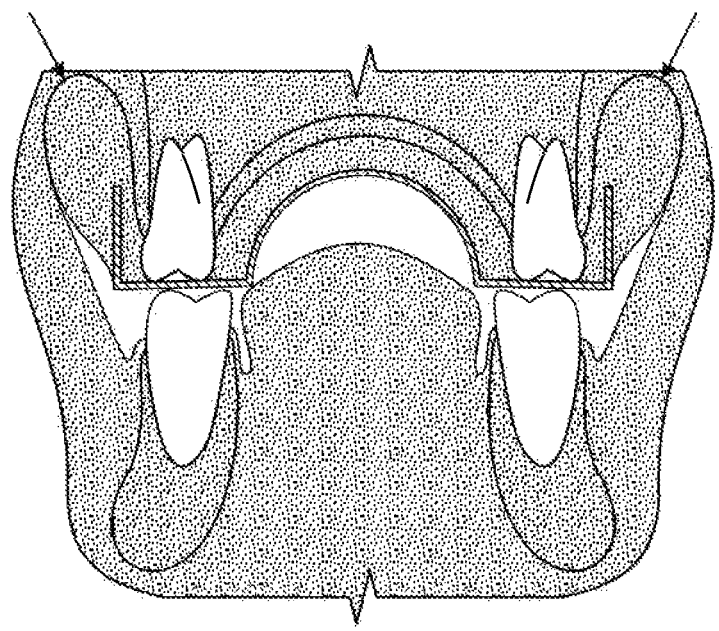
FIGS. 29A-29B illustrate cross-sectional views of impressions placed according to an embodiment of the present invention after impression material has been forced into the vestibules.
Figure 29B:
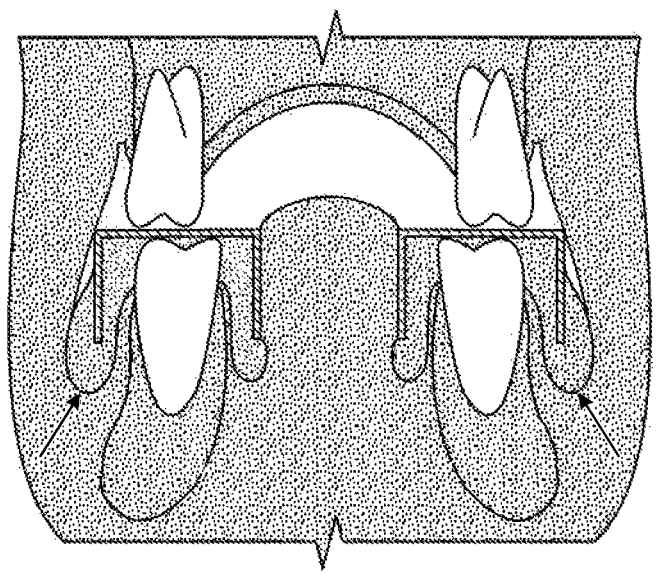

Contrary to the conventional techniques, the intent of the Hydraulic Pressure Dental Impression Technique is to force the base impression material 2715 as deeply as possible into the vestibules (including the upper buccal vestibules 2605, the lower buccal vestibules 2610, and the lingual vestibules 2615). Forcing the base impression material 2715 into the vestibules as disclosed herein allows a seal to be created while taking the wash impression (thereby creating a closed system and hydraulic pressure). As disclosed above, the Hydraulic Pressure Dental Impression Technique for taking the base impression includes: having the patient open their mouth; the operator placing the impression tray filled with base impression material over the tops of the teeth; the operator pushing the impression only slightly over the tops of the teeth (shown in FIG. 8A and FIG. 16A); the operator continuing to hold the handle of the tray to keep it in place; the patient biting down firmly on the stock impression tray. Because of the strong power of the patient's biting muscles, the patient can easily force the impression to seat fully until the teeth have fully penetrated through the dense base impression material and hit the impression tray (shown in FIGS. 28A and 28B). Because the tray seats fully, the sides of a stock tray will extend into the vestibules more deeply and could therefore impinge on the soft tissues of the mouth. The impression tray therefore, can be approximately one size larger (wider) than the stock tray used with other techniques to advantageously avoid impinging on the soft tissues of the mouth. Alternatively, a stock tray can be customized as disclosed herein using a torch with a flame with a fine tip to soften and push the sides of the stock impression tray wider (shown in FIG. 2).

Given that the Hydraulic Pressure Dental Impression Technique generally extends the base impression material 2715 as deeply as possible into the vestibules, the base impression material 2715 can extend beyond the supporting sides of the impression tray (such as the impression tray outer retaining wall 108) (shown in FIGS. 28, 29, 30B and 30D). To achieve the necessary strength and rigidity without support from the sides of an impression tray, the base impression material 2715 in the vestibules (particularly upper buccal vestibules 2605 and lower buccal vestibules 2610) can advantageously have additional thickness. As is illustrated in FIGS. 28A and 28B and FIGS. 30B and 30D, using a wider impression tray can facilitate achieving a greater thickness of base impression material 2715 in the vestibules (particularly upper buccal vestibules 2605 and lower buccal vestibules 2610) (denoted by the double-ended arrows). Because the impression tray can be bitten down on fully, there is little to no bulk of base impression material 2715 between the biting (or occlusal) surface 2711 of the teeth and the roof of the stock impression tray 2713 as is illustrated in FIGS. 28A and 28B. This means that as the patient bites the impression fully, the base impression material 2715 is forced out of the impression tray into the vestibules (including the upper buccal vestibules 2605, lower buccal vestibules 2610, and lingual vestibules 2615). Therefore, much more bulk of impression material 2715 can be found in the upper buccal vestibules 2605, lower buccal vestibules 2610, and the lingual vestibules 2615 (FIGS. 28A and 28B) when using the Hydraulic Pressure Dental Impression Technique. Furthermore, as the patient bites the impression tray to seat it fully, the mouth closes and slacks the cheeks 2645 which can render it easier to stretch the vestibules (2605, 2610, and 2615) to make more room in the vestibules (2605, 2610, and 2615) for the excess base impression material 2715 being forced out. Because the impression tray is bitten down on fully, the sides of the impression tray extend more deeply into the vestibules (2605, 2610, and 2615) (shown in FIGS. 28A and 28B) and force a larger volume of excess base impression material 2715 out of the impression tray and into the vestibules (2605, 2610, and 2615). The cheeks 2645 and lips (not shown) are able to easily stretch in the vestibular area because the mouth is closed and the cheeks 2645 and lips (not shown) are not stretched. Because of the deeper extent into the vestibules (2605, 2610, and 2615) of the sides of the impression tray, a larger volume of base impression material 2715 can be pushed out of the tray and into the vestibules (2605, 2610, and 2615), and due to the ability of the vestibules (2605, 2610, and 2615) to stretch, the base impression material 2715 can generally extend far deeper into the vestibules (2605, 2610, and 2615) as is illustrated in FIGS. 28A, 28B, 29A and 29B.

The tongue 2650 is a very strong muscle and is therefore very resistant to being pushed away as the excess base impression material 2715 is forced into the lingual vestibules 2615. Consequently, the base impression material can be advantageously directed more deeply into the elastic lingual vestibules 2615 (shown in FIG. 28B).

Figure 10:
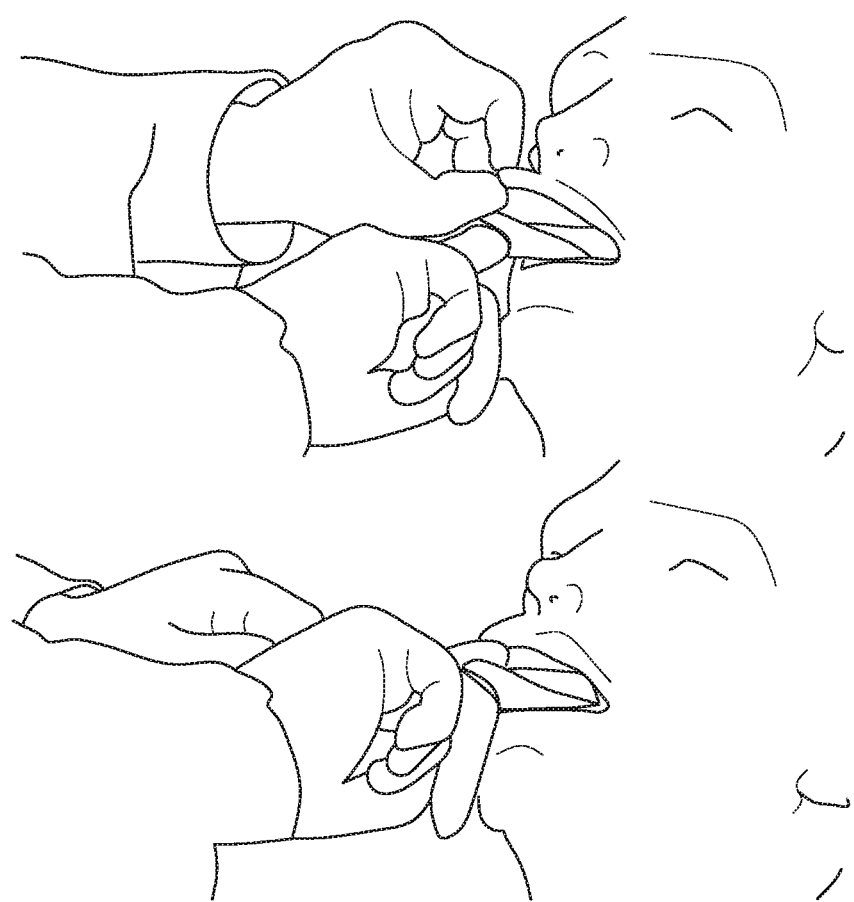
FIG. 10 illustrates the use of a finger to properly push base impression putty into the upper right buccal vestibule of a patient.
Figure 11:
FIG. 11 illustrates the use of a finger to properly push base impression putty into the upper anterior vestibule of a patient.

When putty is the base impression material 2715, the base impression can be forced even more deeply into the buccal vestibules by the following: instructing the patient to keep gently biting on the impression which keeps the mouth closed and the lips and cheeks un-stretched and relaxed; and the operator placing a finger, or other instrument, under the patient's lips and cheeks and pushing the bulk of the base impression putty even more deeply into the buccal vestibules (as illustrated in FIGS. 9-11). This technique causes the putty 702 of FIG. 7 to go tighter and deeper into the vestibules (including, namely, the upper buccal vestibules 2605 and the lower buccal vestibules 2610) because the cheeks 2645 are not stretched at this point and will easily stretch much more when the finger pushes the impression putty 702 more deeply into the vestibules (2605, 2610, and 2615) (shown in FIGS. 29A and 29B, denoted by the black arrows). As is illustrated in FIGS. 29A, 29B, 30B and 30D the putty 702 can hold its shape, even in the vestibules (2605, 2610, and 2615), when the finger is removed from the mouth because the putty 702 has a very dense consistency.

When a strong force is applied to seat the impression (e.g., the patient bites firmly on the impression), base impression putty 702 can be pushed between the teeth. The base impression putty 702 becomes very rigid after fully setting, therefore the putty 702 base impression can be quite difficult to remove from the patient's mouth once the putty 702 is fully set. To prevent difficulty of removal, as discussed above, before the putty 702 impression material hardens, the impression can be loosened and very slightly lifted off the teeth then bitten back into place. This action can pull the putty 702 from between the teeth enough to render the impression easier to remove once the putty 702 has set.

Figure 31A:
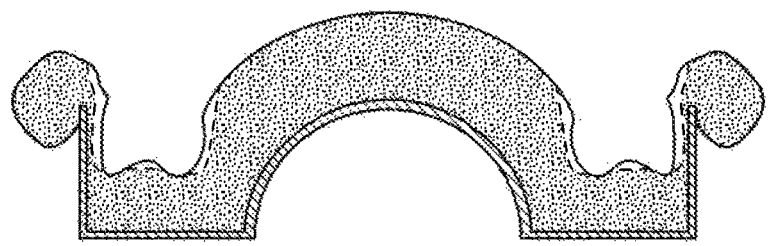
FIGS. 31A and 31C illustrate cross-sectional views of base impressions, taken using conventional impression techniques, that have been prepared for taking a wash impression.
Figure 31B:
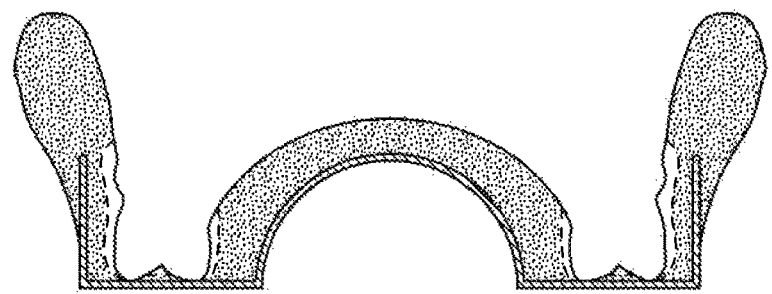
FIGS. 31B and 31D illustrate cross-sectional views of base impressions, taken using a method according to an embodiment of the present invention, that have been prepared for taking a wash impression.
Figure 31C:
Figure 31D:
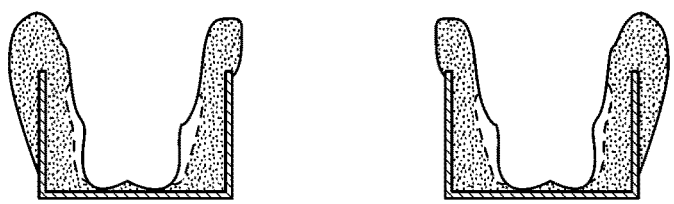
Figure 33A:
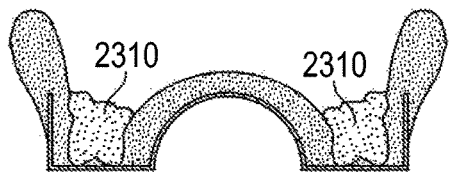
FIGS. 33A-33D illustrate cross sectional views of base impressions, taken using a method according to an embodiment of the present invention, that have been filled with wash impression material.
Figure 33B:
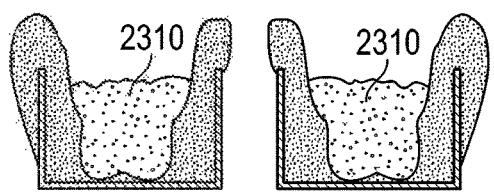
Figure 33C:
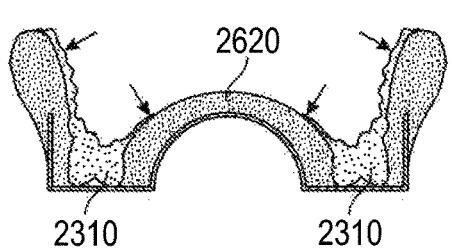
Figure 33D:
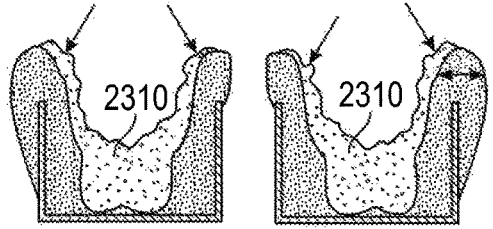

To provide space for the lower viscosity second layer of impression material (the light body wash impression material 2310), the base impression can be ground out in the area of the teeth and gums. When using the conventional impression technique, the impression does not routinely extend deeply into the vestibule; therefore it becomes necessary to grind out the entire internal surface of the impression as is illustrated in FIGS. 31A and 31C (denoted by the dashed lines). Conversely, when using the Hydraulic Pressure Dental Impression Technique, only the teeth and gum areas should be ground out as illustrated in FIGS. 31B and 31D (denoted by the dashed lines): there is a deep area extending into the vestibule which is not ground out. With the conventional technique, low viscosity light body wash impression material 2310 is loaded into the base impression, thereby filling the tooth area of the impression (shown in FIGS. 32A and 32C, denoted by the heavy arrows). Upon inserting such a conventional impression loaded with light body wash impression material 2310 into a patient's mouth and seating it on the teeth (as illustrated in FIGS. 32B and 32D), the base material does not seal in the vestibular area. The base impression material was ground away and the elastic cheek tissue easily stretches to allow an easy escape (or an open system) of light body wash impression material 2310 (shown in FIGS. 32B and 32D, denoted by the heavy arrows). Therefore, very little hydraulic pressure is created as the impression is seated. Conversely, when using the Hydraulic Pressure Dental Impression Technique, low viscosity light body wash impression material 2310 is loaded into the base impression, slightly over-filling the tooth areas of the impression (shown in FIGS. 33A and 33B). The light body wash impression material 2310 is then pushed up the sides of the internal surface of the base impression, all the way up to the full extent of the vestibular extensions (or fully into the vestibules 2605, 2610, and 2615), and half way up the sides of the palate 2620 (shown in FIGS. 33C and 33D, denoted by the heavy arrows). By pushing the light body wash impression material 2310 up the internal sides of the impression, as the impression is inserted over the patient's teeth, the light body wash impression material 2310, being of significantly higher density than air, forms a gasket (i.e., a seal) between the internal side of the base impression (where it was not ground out) and the oral mucosa, thereby closing the system. That seal remains sealed because the base impression was previously pushed firmly against the vestibular tissues overlying the jaw bones. Therefore, when hydraulic pressure is created, this area has very little ability to further compress.

Figure 33E:
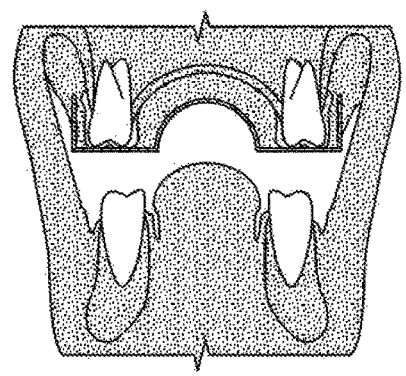
FIGS. 33E-33F illustrate cross-sectional views of the wash impression material-filled base impressions of FIGS. 33A-33D placed in the mouth according to an embodiment of the present invention.
Figure 33F:
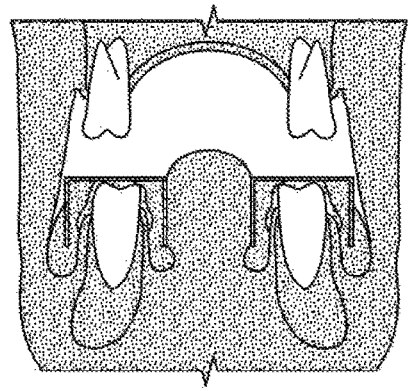

When the base impression loaded with light body wash impression material 2310 is inserted into the patient's mouth, it is seated over the teeth with significant force, generated by the operator's hand. The force is exerted for some amount of time (representative ranges being herein disclosed) after which the impression is held gently in place until set as shown in FIGS. 33E and 33F. The force generated by the operator combined with the sealed/closed system, creates significant hydraulic pressure within the impression on the light body wash impression material 2310, thereby advantageously achieving precise detail. Given that the pressure within a closed system is equal across all locations, this serves to achieve greater accuracy across the entirety of the impression.

To create hydraulic pressure, a closed system must be achieved—the more closed the system, the higher is the level of hydraulic pressure which can be created. Pascal's Principle states that within a closed system, a pressure applied to any part of a confined fluid (or flowable material) transmits equally to every other part with no loss of pressure (the pressure acts with equal force on all equal areas of the confining walls and perpendicular to the walls). Therefore, the force on the low viscosity light body wash impression material 2310 exerts pressure in all directions (is omni-directional) as opposed to the uni-directional pressure exerted in conventional impression techniques. The omni-directional hydraulic pressure created by the Hydraulic Pressure Dental Impression Technique combined with the low viscosity of the light body wash impression material 2310 allows the light body wash impression material 2310 to be forced into even the smallest of structures with impeccable detail. Additionally, the hydraulic pressure serves to quickly force out air, thereby preventing the formation of bubbles and voids within the impression.

The Hydraulic Pressure Dental Impression Technique allows the creation of dental impressions with high levels of detail reproducibly superior to those produced using conventional techniques. Such highly detailed dental impression created using embodiments of the invention disclosed herein can be used to create models or replicas. To create a highly detailed replica or model from an impression, simply fill the impression with a casting material, let the casting material harden, and remove the hardened cast or model. In some embodiments, plaster is used as a casting material. In other embodiments, any other appropriate casting material is used.

Figure 34A:
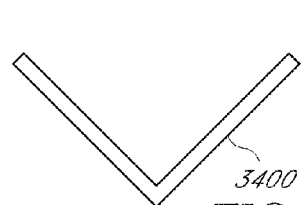
FIGS. 34A-34I illustrate a method of taking an impression of an object according to an embodiment of the present invention.
Figure 34B:
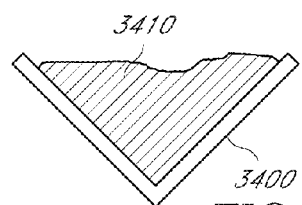

Some embodiments of the present invention can be used to take impression of a portion of an oral cavity, a tooth, two or three teeth, multiple teeth, all the teeth of a jaw, dental appliances, or a dental implant abutment. At least some embodiments of the present invention can be used to take impressions of objects other than a portion of an oral cavity, a tooth, two or three teeth, multiple teeth, all the teeth of a jaw, dental appliances, or a dental implant abutment. FIGS. 34A-34I illustrate a method of taking an impression of a generic object according to an embodiment of the present invention. FIG. 34A illustrates one embodiment of an impression tray 3400. In some embodiments, impression trays can be shaped like the teeth in a jaw (as shown in FIG. 1). In some embodiments, impression trays can be shaped in any configuration that allows the tray to hold an impression material, such as the triangular trough (or v-shaped) impression tray 3400 shown in FIG. 34. To take an impression of an object 3450, first provide an impression tray 3400. Next, fill the impression tray 3400 with a first impression material 3410. The first impression material 3410 can be of a relatively high density, such as a putty or gum-like consistency. The impression tray 3400 can be filled with a sufficient amount of the first impression material 3410 that the entire surface of interest (portion of which an impression is desired) of the object 3450 can be covered, or pressed into the first impression material 3410. FIG. 34B illustrates an impression tray 3400 filled with a first impression material 3410. In some embodiments, it is desirable to fill the impression tray 3400 with sufficient first impression material 3410 that upon taking an impression of the object 3450 (i.e., pressing the object 3450 into the first impression material 3410) that the first impression material 3410 is pushed up past the edges of the impression tray 3400 and "spills over" those edges (shown in FIG. 34C).

Figure 34C:
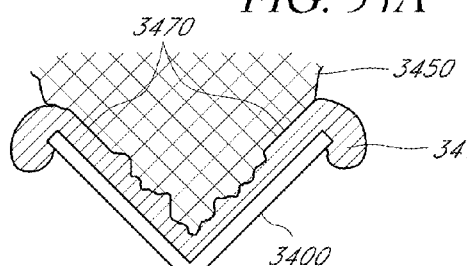
Figure 34D:
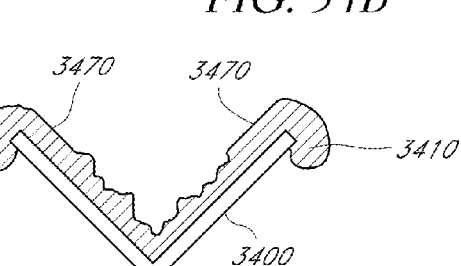

To take the first impression, the object 3450 is pushed with force into the first impression material 3410 which is being held by the impression tray 3400. Alternatively, in some embodiments, the first impression material 3410 which is being held by the impression tray 3400 is pushed with force onto the object 3450. In some embodiments, the object 3450 is pushed into the first impression material 3410 until the surface of the object 3450 hits the surface of the impression tray 3400. In other embodiments, the object 3450 is pushed into the first impression material 3410 less deeply, leaving some depth of first impression material 3410 between the surface of the object 3450 and the surface of the impression tray 3400. FIG. 34C illustrates an object 3450 of which a first impression is being taken: the object 3450 has been pushed into the first impression material 3410 to a depth where some of the first impression material 3410 is left between the surface of the object 3450 and the surface of the impression tray 3400. In some embodiments, the object 3450 can be left in the first impression material 3410 until the first impression material 3410 has just begun to set. In other embodiments, the object 3450 can be left in the first impression material 3410 until the first impression material 3410 is fully set. As discussed above, with respect to FIG. 12A, to ease removal of the object 3450 once the first impression material 3410 has hardened sufficiently, it may be useful to loosen the object 3450 (before the first impression material 3410 has fully set) as if it was being removed then push the object 3450 back into place. In some embodiments, the object 3450 is lifted off only once, twice or more, three times or more, four times or more, or more than five times consecutively. In some embodiments, the object 3450 may not require lifting off at all. FIG. 34D illustrates an impression of the object 3450 after the object 3450 has been removed and the first impression material 3410 is fully set or hardened. As can be seen from the figure, the first impression material 3410, held by the impression tray 3400 produces a negative impression of the object 3450.

Figure 34E:
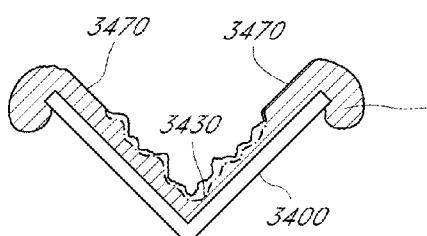
Figure 34F:
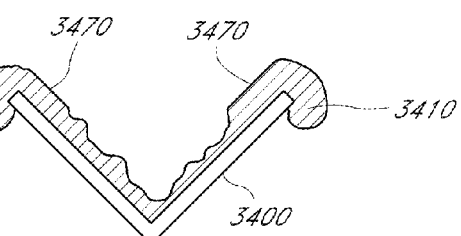

To prepare for taking the second impression, details can be removed from the first impression. FIG. 34E illustrates a details on a first impression which can be removed down to dotted line 3430. In some embodiments, details can be removed from the first impression by using a grinding bur. In other embodiments, details can be removed from the first impression by any method capable of removing set first impression material 3410 from the surface of the first impression. In some embodiments, sealing surfaces 3470 are left untouched (not ground down or removed) as shown in FIG. 34E. In some embodiments, the presence of sealing surfaces 3470 allows the creation of a seal, a closed system, and hydraulic pressure in a subsequent second impression. FIG. 34F illustrates a first impression which has been prepared for taking a second impression by grinding out details of the first impression and having sealing surfaces 3470. As discussed above, in some embodiments, the inner surface(s) of the first impression can be remove or relieved in the range of about 0.1-1.0 mm deep, about 0.2-0.9 mm deep, about 0.3-0.8 mm deep, and about 0.4-0.7 mm deep, including about 0.5 mm deep or any other depth which appropriately prepares the aforementioned surfaces. By comparing FIG. 34D to FIG. 34F, it can be seen that a first impression properly prepared for taking a second impression has the same general shape as the object 3450 but much less detail than the object 3450 and leaves the sealing surfaces 3470 untouched.

Figure 34G:
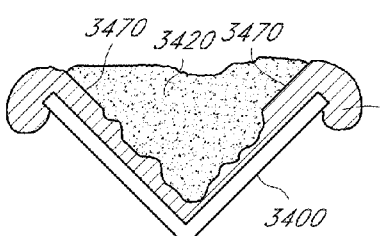

To prepare for taking the second impression, begin by filling the prepared first impression with a second impression material 3420. The second impression material 3420 can be of a relatively low density by comparison to the first impression material 3410 (e.g., a toothpaste-like or honey-like consistency). The prepared first impression can be filled with a sufficient amount of the second impression material 3420 that the entire surface of interest (portion of which an impression is desired) of the object 3450 can be covered, or pressed into the second impression material 3420. In some embodiments, the prepared first impression can be completely filled with the second impression material 3420 as shown in FIG. 34G. In other embodiments, the prepared first impression can be coated with the second impression material 3420 in a depth only slightly deeper than the depth of the first impression material 3410 that was removed (illustrated by dotted line 3430 in FIG. 34E) (not shown). In some embodiments, it is desirable to fill the first impression with sufficient second impression material 3420 that upon taking the second impression of the object 3450 (i.e., pressing the object 3450 into the prepared first impression filled (in some fashion) with second impression material 3420) that the second impression material 3420 is pushed up past the edges of the prepared first impression and "spills over" those edges (shown in FIG. 34H).

Figure 34H:
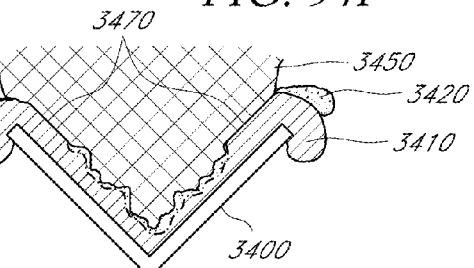
Figure 34I:
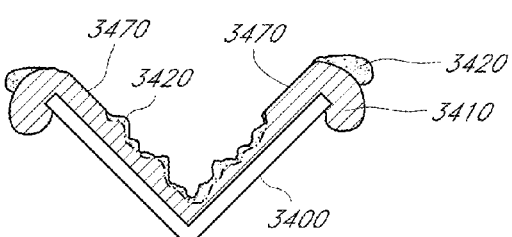

To take the second impression, the object 3450 is pushed with force into the second impression material 3420 which is being held by the prepared first impression. The object 3450 is pushed with force until the object 3450 contacts the sealing surfaces 3470 of the prepared first impression. FIG. 34H illustrates an object 3450 of which a second impression is being taken: the object 3450 has been pushed into the second impression material 3420 until it abuts the sealing surfaces 3470. The object 3450 can be held in place with force until the second impression material 3420 has set sufficiently. In some embodiments, the object 3450 can be held with force in the second impression material 3420 until the second impression material 3420 has just begun to set. In other embodiments, the object 3450 can be held with force in the second impression material 3420 until the second impression material 3420 is fully set. FIG. 34I illustrates an impression of the object 3450 after the object 3450 has been removed and the second impression material 3420 is fully set or hardened. As can be seen from the figure, the second impression material 3420, held by the prepared first impression produces a highly accurate negative impression of the area or portion of interest of object 3450.

Such a two-step method of making an impression can allow the creation of a highly detailed negative impression of an object 3450. Leaving sealing surfaces 3470 on the first impression and removing one or more details of the first impression allows the creation of a closed system for the second impression. A closed system can allow the creation of hydraulic pressure on the lower density second impression material 3420 which causes the lower density second impression material 3420 to be forced against the object 3450 in an omnidirectional fashion thereby permitting high levels of detail.

Of course, the foregoing description is of certain features, aspects and advantages of the present invention, to which various changes and modifications can be made without departing from the spirit and scope of the present invention. Thus, for example, those of skill in the art will recognize that the invention can be embodied or carried out in a manner that achieves or optimizes one advantage or a group of advantages as taught herein without necessarily achieving other objects or advantages as can be taught or suggested herein. In addition, while a number of variations of the invention have been shown and described in detail, other modifications and methods of use, which are within the scope of this invention, will be readily apparent to those of skill in the art based upon this disclosure.

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions (e.g., by excluding features or steps from certain embodiments, or adding features or steps from one embodiment of a system or method to another embodiment of a system or method). Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "load(ing) or fill(ing) the base impression with the light body wash impression material" include "instructing the load(ing) or fill(ing) the base impression with the light body wash impression material." The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers, and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A method of producing an impression of at least one tooth of a patient, comprising:
   providing an impression tray;
   providing a first impression material;
   filling the impression tray with the first impression material;
   taking a first impression of the at least one tooth to create a cavity corresponding to a dimension of the at least one tooth, wherein the first impression of the at least one tooth is taken using the impression tray filled with the first impression material, wherein the first impression material is forcibly placed to extend beyond the at least one tooth, such that the first impression material extends past a gingival margin of the patient and into a vestibule of the patient to form a sealing surface in the vestibule of the patient;
   enlarging a dimension of the cavity corresponding to a dimension of the at least one tooth substantially without enlarging a dimension of the first impression material that was forcibly placed to extend beyond the at least one tooth;
   providing a second impression material;
   filling the first impression of the at least one tooth with the second impression material;
   taking a second impression of the at least one tooth to create a cavity corresponding to a dimension of the at least one tooth, wherein the second impression of the at least one tooth is taken using the first impression of the at least one tooth after enlarging a dimension of the cavity filled with the second impression material and wherein the first impression material that was forcibly placed to extend beyond the at least one tooth is configured to retain the second impression material within the enlarged cavity corresponding to a dimension of the at least one tooth using the sealing surface in the vestibule of the patient and thereby substantially increase a hydraulic pressure on the second impression material within the enlarged cavity.

2. The method of claim 1, wherein taking a first impression includes instructing a patient to bite down on the impression tray filled with the first impression material.

3. The method of claim 1, wherein the at least one tooth includes a dental implant abutment.

4. The method of claim 3, wherein forcibly placing the first impression material to extend beyond the dental implant abutment includes pushing the first impression material into one or more of the upper buccal vestibules, the lower buccal vestibules, and the lingual vestibules.

5. The method of claim 1, wherein the impression tray is customized prior to use.

6. The method of claim 5, wherein the customization is accomplished by heating and bending the impression tray.

7. The method of claim 1, wherein the first impression material has a first density and the second impression material has a second density, wherein the first density is higher than the second density.

8. The method of claim 7, wherein the first impression material is selected from one of heavy impression putty and heavy body impression material.

9. The method of claim 1, wherein the filling the impression tray with the first impression material includes filling the impression tray to or past the top of the impression tray.

10. The method of claim 1, wherein forcibly placing the first impression material to extend beyond the at least one tooth includes pushing the first impression material into one or more of the upper buccal vestibules, the lower buccal vestibules, and the lingual vestibules.

11. The method of claim 10, wherein the forcibly placing includes using a finger to push the first impression material.

12. The method of claim 10, wherein the forcibly placing includes using a tool to push the first impression material.

13. The method of claim 1, wherein the enlarging a dimension of the cavity includes grinding away at least some detail from the inner surface of the first impression.

14. The method of claim 13, wherein the at least some detail includes the interproximals.

15. The method of claim 1, wherein a dimension of the cavity corresponding to a sealing surface of the first impression is not enlarged.

16. The method of claim 15, wherein the sealing surface corresponds at least to a portion of the first impression extending beyond the at least one tooth.

17. The method of claim 15, wherein the sealing surface corresponds at least to a portion of the first impression extending into one or more of the upper buccal vestibules, the lower buccal vestibules, and the lingual buccal vestibules.

18. The method of claim 1, wherein the filling the first impression with the second impression material includes coating an inner surface of the cavity with the second impression material, wherein the coating is about as deep as a deepest external feature of the at least one tooth.

19. A system for casting a model of at least one tooth of a patient, comprising:
    an impression of the at least one tooth, wherein the impression was created using a first impression step and a second impression step, wherein the first impression step includes:
        filling an impression tray with a first impression material;
        taking a first impression of the at least one tooth to create a cavity corresponding to a dimension of the at least one tooth, wherein taking the first impression includes forcibly pushing the first impression material into an oral structure extending beyond the at least one tooth, such that the first impression material extends past a gingival margin of the patient and into a vestibule of the patient to form a sealing surface in the vestibule of the patient;
        removing the first impression;
        enlarging at least one dimension of the cavity without removing impression material from the portion of the first impression corresponding to the oral structure extending beyond the at least one tooth and forming the sealing surface;
    wherein the second impression step includes:
        filling the first impression with a second impression material;
        taking a second impression of the at least one tooth to create a cavity corresponding to a dimension of the at least one tooth, wherein the impression is taken using the first impression filled with the second impression material, and wherein the sealing surface, formed by the first impression material extending into the vestibule of the patient, past the gingival margin of the patient, is configured to retain the second impression material within the cavity corresponding to a dimension of the at least one tooth and generate a high hydraulic pressure thereon; and
        removing the second impression;
    and;
    a casting material.

* * * * *